(12) United States Patent
Potter

(10) Patent No.: US 6,214,569 B1
(45) Date of Patent: Apr. 10, 2001

(54) METHODS FOR SCREENING FOR INHIBITORS OF ALZHEIMER β-PEPTIDE FILAMENT FORMATION

(75) Inventor: Huntington Potter, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 08/914,694

(22) Filed: Aug. 19, 1997

Related U.S. Application Data

(62) Continuation of application No. 08/417,937, filed on Apr. 6, 1995, now Pat. No. 5,780,587, which is a continuation-in-part of application No. 08/328,491, filed on Oct. 25, 1994, now abandoned, which is a continuation-in-part of application No. 08/290,198, filed on Aug. 15, 1994, now abandoned, which is a continuation-in-part of application No. 08/179,574, filed on Jan. 10, 1994, now Pat. No. 5,506,097, which is a continuation-in-part of application No. 07/819, 361, filed on Jan. 13, 1992, now Pat. No. 5,338,663, which is a continuation-in-part of application No. 07/572,671, filed as application No. PCT/US93/00325 on Jan. 13, 1993, now abandoned.

(51) Int. Cl.$^7$ ..............................................................

(52) U.S. Cl. ............................................................ 435/7.8

(56) References Cited

U.S. PATENT DOCUMENTS

| 4,303,592 |   | 12/1981 | Laura et al. . |
| 4,666,829 |   | 5/1987  | Glenner et al. . |
| 5,604,102 | * | 2/1997  | McConlogne et al. . |
| 5,854,204 | * | 12/1998 | Findeis et al. . |

FOREIGN PATENT DOCUMENTS

| 2071661   | 9/1981 | (GB) . |
| WO 91/13904 | 9/1991 | (WO) . |
| WO 92/03474 | 3/1992 | (WO) . |
| WO 92/03542 | 3/1992 | (WO) . |
| WO 93/15112 | 8/1993 | (WO) . |
| WO 94/09364 | 4/1994 | (WO) . |

OTHER PUBLICATIONS

Gallo et al, Am. J. Pathology 145(3):526–530, Sep. 1994.*
Levine, Protein Science 2(3):401–410, 1993.*
W. J. Strittmatter, et al., "Binding of Human Apolipoprotein E to Synthetic Amyloid β Peptide: Isoform–Specific Effects and Implications for Late–Onset Alzheimer Disease," *Proc. Natl. Acad. Sci. USA,* 90:8098–8102 (1993).
Fraser, P. E., et al., "$α_1$–Antichymotrypsin Binding to Alzheimer Aβ Peptides Is Sequence Specific and Induces Fibril Disaggregation In Vitro," *J. of Nurochem.,* 61(1):298–305 (1993).
Nelson, R. B. and Siman, R., "Clipsin, a Chymotrypsin–Like Protease in Rat Brain Which is Irreversibly Inhibited by α–1–Antichymotrypsin," *J. of Biol. Chem.,* 265(7):3836–3842 (1990).

Nelson, R. B. and Siman, R., "Clipsin, a Chymotrypsin–Like Protease in Rat Brain Which is Irreversibly Inhibited by α–1–Antichymotrypsin," *J. of Biol. Chem.,* 266(19):12796 (1991).
Abraham, C. R., et al., "A Calcium–Activated Protease From Alzheimer's Disease Brain Cleaves at the N–Terminus of the Amyloid β–Protein," *Biochem. and Biophys. Research Comm.,* 174(2):790–796 (1991).
Neve, R. L. and Potter, H., "Molecular Biology of Alzheimer Amyloid Plaque Proteins," In Brosus, Jugel and Freman, Robert T. (ed.), *Molecular Genetic Approaches to Neuropsychiatric Disease,* (Academic Press Inc., San Diego) pp. 281–305 (1991).
Potter, H., et al., "The Two Alzheimer Amyloid Components $α_1$–Antichymotrypsin and β–Protein Form a Stable Complex In Vitro" *Neurobiol. of Aging,* 11(3):245 (1990).
Potter, H., et al., "The Alzheimer Amyloid Components $α_1$–Antichymotrypsin and β–Protein Form a Stable Complex In Vitro," In K. Iqbal, et al. (Ed.), *Alzheimer's Disease: Basic Mechanisms, Diagnosis and Therapeutic Strategies* (NY: John Wiley & Sons Ltd.), pp. 275–280 (1991).
Yanker, B. A., et al., "Neurotrophic and Neurotoxic Effects of Amyloid β Protein: Reversal by Tachykinin Neuropeptides," *Science,* 250:279–282 (1990).
Whitson, J. S., et al., "Amyloid β Protein Enhances the Survival of Hippocampal Neurons In Vitro," *Science,* 243:1488–1490 (1989).
Potter, H. et al., "The Involvement of Proteases, Protease Inhibitors, and an Acute Phase Response in Alzheimer's Disease," *Annals NY Acad. Sci.* pp. 161–173 (1992).
Kayyali, U. S. et al., "Characterization of Amyloid Precursor Protein–Associated Serine Esterase Activity in Different Cell Lines," [From *Society for Neuroscience Abstracts,* 19(2)], 23rd Annual Meeting, Washington, D.C., Nov. 7–12 (1993), Abstract 669.7.
Kayyali, U. S., et al., "Identification of Adrelase–A Serine Hydrolase Intrinsic to the Alzheimer Amyloid Precursor Protein," *Advances in Biosciences,* 87:221–222 (1993).

(List continued on next page.)

Primary Examiner—Patricia A. Duffy
(74) Attorney, Agent, or Firm—Hamilton, Brook, Smith & Reynolds, P.C.

(57) ABSTRACT

Methods of treating an individual with Alzheimer's Disease by administering to the patient a therapeutically effective dose of a compound which interferes with the interaction between Alzheimer β-protein and Apolipoprotein E4 or $α_1$-antichymotrypsin, thereby suppressing the formation of Alzheimer β-protein filaments and the neurotoxic effects of these filaments. The present invention also refers to methods of screening for compounds which are effective drugs for treating Alzheimer's disease. These methods comprise screening for compounds which suppress the formation of Alzheimer β-protein filaments in the presence of promoting factors and which suppress the neurotoxic effects of these filaments formed in the presence of promoting factors.

8 Claims, 12 Drawing Sheets

OTHER PUBLICATIONS

Abraham, C. R., et al., "Immunochemical Identification of the Serine Protease Inhibitor $\alpha_1$-Antichymotrypsin in the Brain Amyloid Deposits of Alzheimer's Disease," *Cell*, 52:487–501, (Feb. 26, 1988).

Dressler, D., et al., *Abstracts of the Society for Neuroscience*, vol. 15, Part 2, p. 1041, Abstract No. 414.20 "In Vitro Studies of the Interaction Between the Alzheimer Components $\alpha_1$-Antichymotrypsin and $\beta$-Protein" (1989).

Abraham, C. R. et al., "$\alpha_1$-Antichymotrypsin Is Associated Soley with Amyloid Deposits Containing the $\beta$-Protein Amyloid and Cell Localization of $\alpha_1$-Antichymotrypsin," *Neurobiol. Aging*, 11(2):123–129 (1990).

Rozemuller, J. M., et al., "Acute Phase Proteins in Amorphous and Classical Plaques; Differences Between Vascular and Plaque Amyloid," *Neurobiol. Aging*, 11:310, Abstract No. 238 (1990).

Kirschner, D. A. et al., "Synthetic Peptide Homologous to $\beta$-Protein from Alzheimer Disease Forms Amyloid–Like Fibrils In Vitro," *Proc. Natl. Acad. Sci. USA*, 84:6963–6957 (1987).

Bugiani, O., et al., "Synaptic Alterations in Preamyloid Deposits,"0 *Neurobiol. Aging*, 11:310, Abstract No. 236 (1990).

Castano, E. M., et al., "In Vitro Formation of Amyloid Fibrils from Two Synthetic Peptides of Different Lengths Homologous to Alzheimer's Disease $\beta$-Protein," *Biochem. Biophys. Res. Commun.*, 141(2):782–789 (1986).

Abraham, C. R., and Potter, H. "Alzheimer's Disease: Recent Advances in Understanding the Brain Amyloid Deposits," *Bio/Technology*, 7:147–153 (1989).

Travis, J., et al., "Human $\alpha$–1–Antichymotrypsin:Interaction with Chymotrypsin–Like Proteinases," *Biochemistry*, 17(26):5651–5656 (1978).

Reconstruction of poster believed to be presented by Dr. Potter at the Second International Conference on Alzheimer's Disease and Related Disorders (Toronto, Canada) Jul. 15–20, 1990 (pp. 1–6).

Reconstruction of poster believed to be presented by Dressler and Potter at the Annual Meeting of the Society for Neuroscience, Oct. 29, 1989 (3 pages).

Namba, Y., et al., "Apolipoprotein E Immunoreactivity in Cerebral Amyloid Deposits and Neurofibrillary Tangles in Alzheimer's Disease and Kuru Plaque Amyloid in Creutzfeld–Jakob Disease," *Brain Research*, 541:163–166 (1991).

Wisniewski, T. and Frangione, B., "Apolipoprotein E: a Pathological Chaperone Protein in Patients with Cerebral and Systemic Amyloid," *Neuroscience Lett. 135*:235–238 (1992).

Pasternack, J. M., et al., "Astrocytes in Alzheimer's Disease Gray Matter Express $\alpha_1$-Antichymotrypsin mRNA," *Am. J. Path.*, 135:827–834 (1989).

Koo, E. H., et al., "Developmental Expression of $\alpha_1$-Antichymotrypsin in Brain May be Related to Astrogliosis," *Neurobiol. Aging*, 12:495–501 (1991).

Rebeck, G. W., et al., "Apolipoprotein E in Sporadic Alzheimer's Disease: Allelic Variation and Receptor Interactions," *Neuron*, 11:575–580 (1983).

Strittmatter, W. J., et al., "Apolipoprotein E: High–Avidity Binding to $\beta$–Amyloid and Increased Frequency of Type 4 Allele in Late–Onset Familial Alzheimer's Disease," *Proc. Natl. Acad. Sci., USA*, 90:1977–1981 (Mar. 1993).

Corder, E. H., et al., "Gene Dose of Apolipoprotein E Type 4 Allele and the Risk of Alzheimer's Disease in Late Onset Families," *Science*, 261:921–923 (Aug. 13, 1993).

Sanan, D. A., et al., "Apolipoprotein E Associates with $\beta$ Amyloid Peptide of Alzheimer's Disease to Form Novel Monofibrils," *J. Clin. Invest.*, 94:860–869 (Aug. 1994).

Schwarzman, A. L., et al., "Transthyretin Sequesters Amyloid $\beta$ Protein and Prevents Amyloid Formation," *Proc. Natl. Acad. Sci., USA*, 91:8368–8372 (Aug. 1994).

Wisniewski, T., et al., Acceleration of Alzheimer's Fibril Formation by Apolipoprotein E In Vitro, *Am. J. Pathol.*, 145:1030–1035 (1994).

Whitson, J. S., et al., "Attenuation of the Neurotoxic Effect of A$\beta$ Amyloid Peptide by Apolioprotein E," *Biochemical and Biophysical Research Communication*, 199(1):163–170 (Feb. 28, 1994).

C.W. Wong et al., "Neuritic Plaques and Cerebrovascular Amyloid in Alzheimer Disease are Antigenically Related," Proc. Natl. Acad. Sci. USA 82:8729–8732 (Dec. 1985).

Smith, C., and Anderton, B. H., "The Molecular Pathology of Alzheimer's Disease: are we any closer to understanding the neurodegenerative process?," *Neuropathology and Applied Neurobiology*, 20:322–338 (1994).

Singh, V. K., "Studies of Neuroimmune Markers in Alzheimer's Disease," *Molecular Neurobiology*, 9(1–3):73–81 (1994).

Cacabelos, R., et al., "Cerebrospinal Fluid Interleukin–1$\beta$ (IL–1$\beta$) in Alzheimer's Disease and Neurological Disorders," *Meth. Find. Exp. Clin. Pharmacol.*, 13(7):455–458 (1991).

Wong, Y.C. et al., "cDNA Cloning of a Novel Cell Adhesion Protein Expressed in Human Squamous Carcinoma Cells," *Biochem. Biophys. Res. Comm. 166*:984 (Jan. 1980).

Glenner, G. G. and Wong, C. W., "Alzheimer's Disease: Initial Report of the Purification and Characterization of a Novel Cerebrovascular Amyloid Protein," *Biochem. Biophys. Res. Comm.*, 120(3):885–890 (May 1984).

Halverson, K. et al., "Molecular Determinants of Amyloid Deposition in Alzheimer's Disease: Conformational Studies of Synthetic $\beta$–Protein Fragments," *Biochemistry 29(11)*: 2639–2644 (Mar. 1990).

Okado H. and Harumasa Okamoto, "A Xenopus Homologue of the Human $\beta$–Amyloid Precursor Protein: Developmental Regulation of its Gene Expression," *Biochem. and Biophys. Res. Comm. 189(3)*:1561–1568 (Dec. 1992).

Mahley, R. W., "Apolipoprotein E: Cholesterol Transport Protein with Expanding Role in Cell Biology," *Science*, 240:623–630 (Apr. 1988).

Mutsumoto, A., "Familial Alzheimer's Disease Cells Abnormally Accumulate $\beta$–Amyloid–Harbouring Peptides Preferentially in Cytosol but not in Extracellular Fluid,", *Eur. J. Biochem. 225*:1055–1062.

\* cited by examiner

| | Column 1 | Column 2 | s.d | % | s.d.2 |
|----|----------|----------|-------|---------|-------|
| 1  | Med only | 2.020 | 0.173 | 100.000 | 8.000 |
| 2  | 12-28 | 2.171 | 0.088 | 104.000 | 4.000 |
| 3  | E4 | 2.011 | 0.136 | 100.000 | 7.000 |
| 4  | AB | 1.242 | 0.064 | 61.000 | 3.000 |
| 5  | AB+E4 | 0.663 | 0.047 | 33.000 | 2.300 |
| 6  | 12-28  0.1nm | 0.691 | 0.001 | 34.000 | 0.000 |
| 7  | 12-28  1nm | 1.011 | 0.100 | 50.000 | 5.000 |
| 8  | 12-28  10nm | 1.287 | 0.064 | 64.000 | 3.000 |
| 9  | 12-28  50nm | 1.711 | 0.064 | 85.000 | 3.000 |
| 10 | 12-28  100nm | 1.769 | 0.097 | 87.000 | 5.000 |
| 11 | 12-28  200nm | 1.737 | 0.003 | 86.000 | 0.000 |
| 12 | 12-28  400nm | 1.748 | 0.049 | 87.000 | 2.400 |
| 13 | 12-28  800nm | 1.739 | 0.187 | 86.000 | 9.000 |

| | Column 1 | Column 2 | s.d | % | s.d.2 |
|---|---|---|---|---|---|
| 1 | Med only | 2.919 | 0.056 | 100.000 | 2.000 |
| 2 | ACT | 3.006 | 0.016 | 102.000 | 1.000 |
| 3 | 2-9 | 2.700 | 0.118 | 95.000 | 4.000 |
| 4 | AB alone | 1.486 | 0.071 | 51.000 | 3.000 |
| 5 | ACT+AB | 0.695 | 0.040 | 24.000 | 1.300 |
| 6 | 2-9 0.1nm | 0.787 | 0.013 | 27.000 | 4.000 |
| 7 | 2-9 1nm | 1.077 | 0.227 | 37.000 | 7.000 |
| 8 | 2-9 10nm | 1.445 | 0.008 | 49.000 | 1.000 |
| 9 | 2-9 50nm | 1.401 | 0.137 | 48.000 | 5.000 |
| 10 | 2-9 100nm | 1.645 | 0.013 | 56.000 | 1.000 |
| 11 | 2-9 200nm | 1.636 | 0.156 | 56.000 | 5.000 |
| 12 | 2-9 400nm | 1.615 | 0.027 | 55.000 | 1.000 |
| 13 | 2-9 800nm | 1.567 | 0.103 | 54.000 | 3.500 |

2-9 dose data 3/25/95

| | Column 1 | % | s.d.2 |
|---|---|---|---|
| 1 | Med only | 100.000 | 6.000 |
| 2 | E2 | 101.000 | 0.000 |
| 3 | E4 | 94.000 | 4.000 |
| 4 | AB | 59.000 | 1.000 |
| 5 | AB+E4 | 30.000 | 2.000 |
| 6 | E2 0.1nm | 30.000 | 2.000 |
| 7 | E2 1nm | 32.000 | 1.000 |
| 8 | E2 10nm | 50.000 | 1.000 |
| 9 | E2 50nm | 84.000 | 3.000 |
| 10 | E2 100nm | 85.000 | 1.000 |
| 11 | E2 200nm | 84.000 | 5.000 |
| 12 | E2 400nm | 85.000 | 5.000 |
| 13 | E2 800nm | 88.000 | 3.000 |

METHODS FOR SCREENING FOR INHIBITORS OF ALZHEIMER β-PEPTIDE FILAMENT FORMATION

RELATED APPLICATIONS

This application is a continuation of U.S. patent application Ser. No. 08/417,937 filed Apr. 6, 1995, now U.S. Pat. No. 5,780,587, which is a Continuation-in-part of U.S. patent application Ser. No. 08/328,491 filed Oct. 25, 1994, now abandoned, which is a Continuation-in-part of U.S. patent application Ser. No. 08/290,198 filed Aug. 15, 1994, now abandoned, which is a Continuation-in-part of U.S. patent application Ser. No. 08/179,574 filed Jan. 10, 1994, now U.S. Pat. No. 5,506,097, which is a Continuation-in-part of U.S. patent application Ser. No. 07/819,361 filed Jan. 13, 1992, now U.S. Pat. No. 5,338,663, which is a Continuation-in-part of U.S. patent application Ser. No. 07/572,671 filed Aug. 24, 1990, now abandoned; priority also is claimed to PCT/US93/00325 filed Jan. 13, 1993.

GOVERNMENT FUNDING

This invention was made with Government support under Contract No. AG08084, AG09665 and GM35967 awarded by NIH. The Government has certain rights in the invention.

BACKGROUND

Alzheimer's disease is a degenerative disorder of the central nervous system that results in a progressive loss of memory and other intellectual functions, such as reasoning, orientation, and judgement (Katzman, R., "Biological Aspects of Alzheimer's Disease," Banbury Report 15, Cold Spring Harbor Laboratory, Cold Spring Harbor, N.Y., (1983)). Alzheimer's disease occurs in sporadic and familial forms and, in the United States, affects about 600 people for every 100,000.

The earliest stages of Alzheimer's disease are characterized by "pre-amyloid" deposits of Alzheimer's β-peptide (Aβ), which are amorphous deposits of Aβ found in many regions of the brain. Aβ is a 39–42 amino acid peptide that is derived from an about 700 amino acid cellular protein of unknown function (Glenner, G. G and Wong, C. G., *Biochem. Biophys. Res. Commun.*, 120:885–890 (1984)). As the disease progresses, neuritic plaques form in the higher centers of the brain, particularly the hippocampus, frontal cortex and amygdala, and also accumulate in the walls of cerebral and meningeal blood vessels more generally. These neuritic plaques consist of mature amyloid deposits which, when viewed in the electron microscope, appear as large numbers of 6–10 nm diameter filaments consisting of Aβ. Amyloid deposits exhibit certain characteristic staining properties (Abraham, C. R. et al., *Cell*, 52:487–501 (1988)).

In addition to Aβ, mature Alzheimer amyloid deposits contain other proteins, in particular the protease inhibitor $\alpha_1$-antichymotrypsin ($\alpha_1$-ACT) (Abraham, C. R. et al., *Cell*, 52:487–501 (1988) and the lipid carrier protein Apolipoprotein E (ApoE) (Namba, Y. et al. *Brain Research*, 541:163 (1991) and Frangione, B., *Neurosci. Lett.* 135:235 (1992)). Surrounding the mature amyloid deposits is a halo of degenerating neurites.

Aβ is apparently derived from a larger membrane-spanning precursor protein whose RNA is alternately spliced to yield several protein products (Seikoe, D. J., *Science*, 248:1058–1060). These observations suggested that the amyloid deposits in Alzheimer's disease could result from abnormal expression or posttranslational modification or processing of a normal molecule. Also intriguing was the finding that the gene encoding the amyloid protein precursor is located on chromosome 21, suggesting a common cause for the deposits observed in Down syndrome, caused by trisomy of chromosome 21, and Alzheimer's disease.

As mentioned above, some cases of Alzheimer's disease appear to be familial, and are inherited in an autosomal dominant fashion. Linkage analysis in four families pointed to a lesion on the long arm of chromosome 21 (St. GeorgeHyslop, P. H. et al., *Science*, 238:664–660 (1987)), which correlated well with the mapping data and similarities between Down syndrome and Alzheimer disease. Recently, hereditary cerebral hemorrhage with amyloidosis of Dutch origin was reported to be linked to the APP gene, and a point mutation in the coding region of the gene was identified (Van Broeckhoven, C. et al., *Science*, 248:1120–1122 (1990); Levy, E. et al., *Science*, 248:1124–1126 (1990)). Patients with this disease have a form of the β-protein in amyloid deposits in meningeal and cerebral blood vessels.

However, other studies reported linkage of familial Alzheimer's disease to a locus on chromosome 21 distinct from the amyloid precursor protein (APP) gene (Tanzi, R. E. et al., *Nature*, 329:156–157 (1987); Van Broeckhoven, C. et al., *Nature*, 329:153–155 (1987)). Furthermore, there was no evidence of duplication of the APP gene in cases of familial or sporadic disease. In fact, studies of some families reportedly indicate no linkage to chromosome 21 (Schellenberg, G. D., *Science*, 241:1507–1510 (1988)). These data suggest that there may be genetic heterogeneity in the cause of inherited forms of Alzheimer's disease, and other locations for the disease gene have been proposed, such as chromosome 14 (Weitkamp, L. R., *Amer. J. Hum. Genet.*, 35:443–453 (1983) and Schellenberg, G. D. et al. *Science*, 258:668 (1992)).

Thus, other components of neuritic plaques that are associated with the mature amyloid deposits may also be of interest and may provide clues to the cause or progress of the disease. These components may also be involved in the neuropathology of the disease and consequently may provide targets for therapeutic drugs which slow the progress or alleviate the symptoms of the disease.

SUMMARY OF THE INVENTION

The present invention relates to methods of screening for drugs which can be used to treat Alzheimer's disease. It further relates to methods of treating an individual with Alzheimer's disease. The present invention also relates to methods of suppressing the formation of neurotoxic Aβ filaments which are present in brain cells of individuals with Alzheimer's Disease and methods of slowing the progression of the disease. It further relates to peptides which suppress the formation of neurotoxic Aβ filaments. The present invention is based, in part, on the discovery that $\alpha_1$-ACT, Apolipoprotein E4 (ApoE4), Apolipoprotein E3 (ApoE3) and Apolipoprotein E2 (ApoE2) promote the assembly of Aβ into amyloid filaments, and that $\alpha_1$-ACT and ApoE4 promote the assembly of Aβ into amyloid filaments which result in neuronal cell death. ApoE4 is the most efficient promoter of the formation of amyloid filament. ApoE2 is the least efficient promoter and even inhibits the formation of amyloid filaments in the presence of Aβ and ApoE4. This invention is also based on the discovery that astrocytes from areas of the brain which are susceptible to developing mature amyloid plaques over-express $\alpha_1$-ACT in the presence of the higher than normal levels of interleukin 1 (IL-1) which are present in the brains of individuals with Alzheimer's disease.

One embodiment of the method of screening is an assay for identifying compounds which slow the formation of Aβ filaments from A: and $\alpha_1$-ACT, Aβ and ApoE3 or Aβ and ApoE4. Another embodiment of the method of screening is an assay for identifying compounds which suppress neuronal cell death in culture in the presence of Aβ and $\alpha_1$-ACT or Aβ and ApoE4. A third embodiment of the method of screening is an assay for identifying compounds which suppress the release of $\alpha_1$-ACT from a culture of astrocytes in the presence of IL-1.

In one embodiment of the method of treating an individual with Alzheimer's disease, a therapeutically effective dose of a compound which interferes with the Aβ/$\alpha_1$-ACT or Aβ/ApoE4 interaction is administered to the individual. In another embodiment of the method of treating an individual with Alzheimer's disease, a therapeutically effective dose of a compound which suppresses neuronal cell death by interfering with the Aβ/$\alpha_1$-ACT or Aβ/ApoE4 interaction is administered to the individual In yet another embodiment of the method of treating an individual with Alzheimer's disease, a therapeutically effective dose of a compound which interferes with the ability of astrocytes from areas of the brain prone to develop mature amyloid plaques to over-express $\alpha_1$-ACT is administered to the patient.

Another embodiment of the present invention refers to a composition comprising Aβ and a promoting factor.

DETAILED DESCRIPTION OF THE INVENTION

Figure 1:
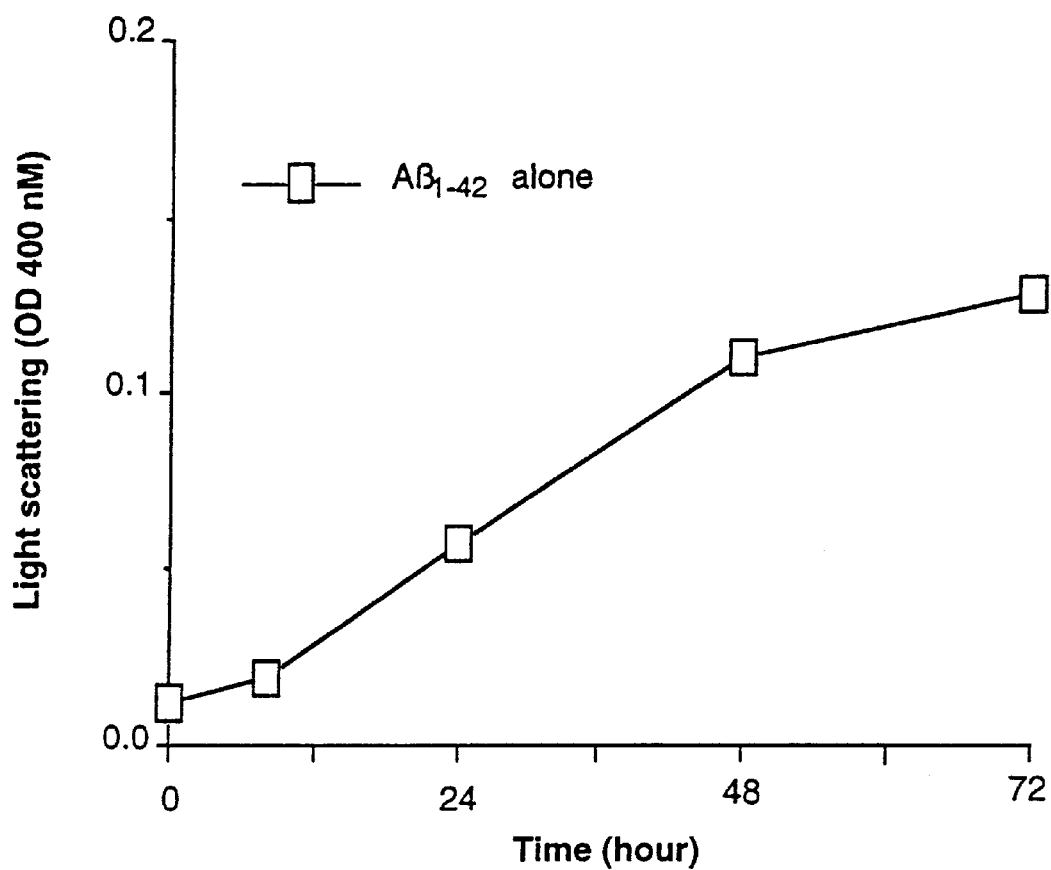
FIG. 1 is a graphic representation of the rate of in vitro formation of Aβ filaments over time from Aβ, as monitored by light scattering.

As described herein, $\alpha_1$-ACT and Apolipoprotein E are not merely incidently associated with mature amyloid plaque that is indicative of Alzheimer's disease. They also promote the formation of Aβ filaments and play a role in causing these filaments to become neurotoxic.

As described in Example 1, Aβ1–42 can spontaneously assemble into high molecular weight amyloid-like filaments in vitro. The formation of these filaments can be monitored by light scattering and electron microscopy, which show that filaments of about 6 nm wide and up to about a few hundred nm long steadily increase in number.

Although Aβ can form amyloid-like filaments spontaneously, such filaments are formed much more rapidly in the presence of the amyloid associated protein $\alpha_1$-ACT, as described in Example 2. In the presence of $\alpha_1$-ACT, filaments form in a matter of hours, rather than days, and can grow to very great lengths, frequently longer than 1 $\mu$M and traversing an entire electron microscope grid square. The diameter of these filaments appears to be identical to those formed by Aβ alone or found in tissue sections from Alzheimer's disease brain. Quantitation by light scattering (which measures the total mass of material in filament form) and by counting random filament crossovers in the electron microscope (a measure of both filament number and length) indicates that $\alpha_1$-ACT accelerates the rate of filament formation at least ten-fold. As soon as eight hours after mixing Aβ and $\alpha_1$-ACT, filament formation appears to reach a maximum under the conditions used in Example 1.

$\alpha_1$-ACT is a serine protease inhibitor. The N-terminal 12 amino acids of Aβ resemble the active site of serine proteases. These structural elements, coupled with enhancement of the rate of Aβ filament formation in the presence of $\alpha_1$-ACT, suggest the formation of a complex between $\alpha_1$-ACT and Aβ. The formation of this complex was demonstrated in the disclosure of U.S. Ser. No. 08/179,574, the contents of which have been expressly incorporated into this application in their entirety. Chymotrypsin is a serine protease which can be inhibited by $\alpha_1$-ACT. U.S. Ser. No. 08/179,574 discloses that a peptide corresponding to amino acids 1–12 or 1–28 of the N-terminal of Aβ peptide (hereinafter referred to as "Aβ$_{1-12}$" and "Aβ$_{1-28}$", respectively) suppress the ability of $\alpha_1$-ACT to inhibit chymotrypsin, while a control peptide from amino acids 258–277 of the Aβ had no effect on $\alpha_1$-ACT activity. Aβ$_{1-12}$ and Aβ$_{1-28}$ form stable complexes with $\alpha_1$-ACT, presumably explaining the inhibitory properties of these peptides. Apparently the N-terminal amino acid residues of Aβ bind with the active site of $\alpha_1$-ACT as a pseudosubstrate, rendering it inaccessible to its normal substrates, such as chymotrypsin. The binding between these two proteins is specific, as evidenced by the ability of the complex to survive harsh treatments, such as boiling in SDS and mercaptoethanol.

ApoE, like $\alpha_1$-ACT, is also present in Alzheimer amyloid deposits and binds tightly to the Aβ protein in vitro. Recent epidemiological studies have indicated that the development of Alzheimer's disease in several families with the "late-onset," inherited form of the disorder depends in part on the particular ApoE alleles carried by the individual. Onset of the disease occurs at a much earlier age in individuals with one or two copies of the ApoE4 allele than in those with the more common Apolipoprotein E3 (ApoE3) allele. Also, genotypes containing the E2 allele are observed less frequently in Alzheimer Disease patients than in control subjects (Corder, et al., *Nature Genetics*, 7:180 (1994)). Consequently, it is of interest to determine precisely what role ApoE4, ApoE3 and ApoE2 have in the etiology of Alzheimer's disease. Accordingly, the ability of purified ApoE4, ApoE3 and ApoE2 to promote Aβ filament formation in vitro was determined. As shown in Examples 3 and 4, ApoE2, ApoE3 and ApoE4 promote Aβ filament formation; the ApoE4 isoform was more active than the ApoE3 or ApoE2 isoform. Electron microscopic examination of the reaction of Aβ with ApoE4 showed the presence of large numbers of long amyloid-like filaments indistinguishable in appearance from those generated in the presence of $\alpha_1$-ACT. Fewer filaments were observed if ApoE3 and ApoE2 were instead added to the reaction. Quantitation of the electron microscopic photographs of filaments confirmed that ApoE4 is most effective in promoting Aβ filament assembly, with $\alpha_1$-ACT and ApoE3 exhibiting intermediate catalytic activity. ApoE2 was the least effective in promoting Aβ filament assembly of the apolipoproteins assessed. Two other Apolipoproteins, ApoAI and ApoAII, were inactive as promoting factors. The conclusions of these experiments are that the two amyloid-associated proteins, $\alpha_1$-ACT and ApoE, particularly the ApoE4 isoform, promote the formation of Aβ filaments from the Alzheimer Aβ peptide in vitro.

The presence of mature amyloid plaques in the brains of Alzheimer patients and the absence of these plaques in disease free individuals suggests that their presence may in some way be responsible for the neuronal cell death that characterizes this disorder. Certain aspects of the present invention are based on the discovery that certain components of mature amyloid plaque, i.e. $\alpha_1$-ACT and ApoE4, are responsible for the formation of Aβ filaments that results in neural cell death. Cell death may result from Aβ filaments that are themselves neurotoxic or from the process by which the Aβ filaments form. This discovery was made by investigating the potential activity of Aβ filaments formed in the presence of $\alpha_1$-ACT, ApoE3 and ApoE4 on human cortical neurons and neuron-like PC-12 cells in culture. As used herein "neuron-like PC-12 cells" are PC-12 cells that have stopped dividing and have differentiated into neuron-like cells as a result of the addition of nerve growth factor (NGF).

Reaction mixtures containing Aβ show minimal neurotoxicity against primary human cortical neurons. However, as described in Example 4, the reaction mixtures containing Aβ and $\alpha_1$-ACT or Aβ and ApoE4 were highly neurotoxic to human cortical neurons after preincubation, whereas the reaction mixtures containing Aβ and ApoE3 were not. Similar increases in neurotoxicity towards neuron-like PC-12 cells were observed with reaction mixtures containing Aβ and ApoE4 or Aβ and $\alpha_1$-ACT. Although the treated cultures showed only minor morphological changes, such as an increase in rounded cells that had become detached from the substrate, a biochemical assay that uses the metabolizable, chromogenic substrate 3,(4,4-dimethylthiazol-2-yl)2,5-diphenyl-tetrazolium bromide (MTT) to quantitatively measure viable cells indicates a strong neurotoxic effect of the filaments formed in vitro. Hansen M. B. et al., *J. Immunol. Methods*, 119:203 (1989). The ApoE3 isoform, which is associated with a much later age of onset of familial Alzheimer's disease, promotes the formation of apparently similar Aβ filaments, but they are not neurotoxic to human cortical neurons. Furthermore, ApoE3, when included in the reaction mixture with Aβ and ApoE4, results in Aβ filaments with considerably reduced neurotoxicity. Separation of the filaments formed in the presence of $\alpha_1$-ACT or ApoE4 from unpolymerized proteins by centrifugation indicated that the filaments (or possibly short, sedimentable oligomers) are the toxic agent. In sum, these results indicate that the amyloid-associated proteins $\alpha_1$-ACT, ApoE4, ApoE3 and ApoE2 promote the formation of neurotoxic Aβ filaments and, thus, can function as pathological chaperones or "promoting factors." As defined herein, "promoting factors" are amyloid associated proteins that, in the presence of Aβ, increase the rate of formation of Aβ filaments. As discussed, neurotoxicity results when Aβ filaments are formed in the presence of certain promoting factors such as $\alpha_1$-ACT and ApoE4.

The presence of proteins other than Aβ in the mature amyloid plaques of Alzheimer's disease has often been thought to represent adventitious binding to already formed Aβ filaments. This hypothesis was reinforced by the finding that synthetic Aβ peptide could, under certain conditions, form filaments spontaneously in vitro. However, the results presented herein clearly show that this hypothesis is incorrect. The ability of $\alpha_1$-ACT and ApoE4 to hasten the formation of Aβ filaments and to cause these filaments to become neurotoxic shows that these proteins do more than merely adventitiously bind to amyloid plaque. Rather, they act as promoting factors to further the progress of the disease and to cause, at least in part, its neurodegenerative symptoms. The molecular mechanism by which $\alpha_1$-ACT and ApoE4 promote neurotoxic Aβ filament formation has yet to be determined, but must involve direct interaction between the participating proteins.

The role which $\alpha_1$-ACT and ApoE4 play as promoting factors in Alzheimer's disease suggests that drugs which block the interaction of these proteins with Aβ can slow the progress of the disease and suppress neurodegeneration. Such drugs can be identified through an assay which measures the ability of a compound to disrupt the interaction among ApoE4, ApoE3, ApoE2, $\alpha_1$-ACT and Aβ. Support for this approach with respect to the Aβ/$\alpha_1$-ACT interaction has been provided by results, presented herein, which show that peptides comprised of Aβ$_{1-12}$ or Aβ$_{1-28}$ block the ability of $\alpha_1$-ACT to inhibit chymotrypsin. These results show that synthetic analogs of Aβ can divert $\alpha_1$-ACT from its harmful interactions. With respect to the interaction between Aβ and ApoE4, the results which show that the formation of Aβ filaments is inhibited when ApoE2 and ApoE4 are incubated with Aβ (FIG. 3 and Example 3) are relevant. Apparently, ApoE2 is able to disrupt the interaction between ApoE4 and Aβ. This result is consistent with the observation that genotypes containing the E2 allele occur less frequently in Alzheimer patients than in controls (Corder, et. al., *Nature Genetics*, 7:180 (1994)). In addition, Aβ filaments assembled from Aβ, ApoE4 and ApoE3 are less neurotoxic than Aβ filaments assembled from only Aβ and ApoE4 are relevant. Apparently, ApoE3 is able to interact with Aβ, thereby blocking the more neurotoxic Aβ/ApoE4 interaction. Furthermore, Aβ filaments promoted by ApoE3 are not neurotoxic, but those promoted by ApoE4 are neurotoxic.

Further support for this method was provided by investigating whether the neurotoxic effects of mixtures of Aβ and proteins which are promoting factors can be blocked by peptides which bind the promoting factors. For example, ApoE4 is thought to bind a peptide comprising amino acid residues 12–28 of Aβ (hereinafter referred to as "Aβ$_{12-28}$"), a region of the peptide predicted to be prone to forming a β-pleated sheet (Strittmatter, et al., *Proc. Natl. Acad. Sci.*

USA, 90:8098 (1993)). A mixture of ApoE4, Aβ and Aβ$_{12-28}$ showed approximately a four-fold reduction in neurotoxicity towards neuron-like PC-12 cells in culture compared with the same cultures of neuron-like PC-12 cells incubated in the absence Aβ$_{12-28}$ (see Example 5 and FIG. 5). Similar results were observed when neuron-like PC-12 cells were incubated with Aβ, α$_1$-ACT and Aβ$_{1-12}$ and compared with the identical PC-12 cultures incubated in the absence of Aβ$_{1-12}$ (see Example 5 and FIG. 6). These results provide support for the use of compounds that interfere with the Aβ/ApoE4 or Aβ/α$_1$-ACT interaction as effective therapeutics which can slow neurodegeneration and the formation of Aβ filaments in an individual with Alzheimer's disease. They also provide the basis for an assay which assesses the ability of compounds to interfere with the interaction between Aβ and these promoting factors and, thus, provides an effective means of identifying such therapeutics.

It has also been discovered that protection against neurotoxocity can be provided by peptides shorter than Aβ$_{1-12}$ and Aβ$_{12-28}$. For example, a 2.0 to 2.4-fold reduction in neurotoxicity is observed when human corticol neurons cells incubated with a mixture of α$_1$-ACT, Aβ and Aβ$_{2-9}$ than when the cells are incubated with a mixture Aβ and α$_1$-ACT alone (Example 12). As described herein, amino acid sequences within Aβ$_{1-12}$ and Aβ$_{12-28}$ (shorter than Aβ$_{12-28}$) are useful for inhibiting respectively, the neurotoxic effects of α$_1$-ACT together with Aβ and Apolipoprotein E4 together with Aβ. In one embodiment, amino acid residues present in Aβ$_{2-9}$, which can be amino acid residues 2–9 or fewer amino acid residues) are useful as inhibitors. However, it is clear that oligopeptides longer than eight amino acids, and indeed longer than twelve amino residues which contain the critical residues can bind α$_1$-ACT and inhibit neurotoxicity. Similarly, oligopeptides both longer than and shorter than Aβ$_{12-28}$ can, if they contain the critical amino acid residues, bind Apolipoprotein E4 and thereby inhibit neurotoxicity.

α$_1$-ACT and ApoE4 are expressed in various parts of the body. For example, the fact that Aβ-containing amyloid deposits that form in the walls of cerebral blood vessels in Alzheimer's disease, Down syndrome and in a cerebral hemorrhage disease (HCHWAD) are all of the mature filamentous form may reflect the ready availability of α$_1$-ACT and ApoE4 in the circulation. However, if α$_1$-ACT and ApoE4 are to act as promoting factors for Alzheimer's disease, they must be expressed in sufficiently high quantities within the brain that they come in contact with Aβ. Within the brains of normal individuals, α$_1$-ACT and ApoE are produced by astrocytes, as evidenced by immunocytochemical analysis (Abraham et al., *Neurobiol. Aging*, 11:123 (1990) and Koo et al., *Neurobiol. Aging*, 12:495 (1991)). However, in situ hybridization, Northern blots, and Western blots have shown that α$_1$-ACT mRNA and protein in astrocytes are greatly increased in those areas of Alzheimer brain prone to amyloid deposition, particularly the hippocampus, frontal cortex and amygdala (Pasternack et al., *Am. J. Path.*, 135:827 (1989), Abraham et al., *Neurobiol. Aging*, 11:123 (1990), Koo et al., *Neurobiol. Aging*, 12:495 (1991) and Rebeck et al., *Neuron*, 11:575 (1993)). These results are consistent with α$_1$-ACT and ApoE4 acting as factors that promote the deposition of mature amyloid plaques, but they do not explain what causes the over-expression of α$_1$-ACT and ApoE4.

Certain aspects of the present invention are based on the discovery that the cytokine interleukin 1 (IL-1), which is over-expressed in Alzheimer's disease, functions to induce α$_1$-ACT expression in human brain astrocytes in culture. Mixed cultures of astrocytes and microglial cells prepared from human fetal brain express α$_1$-ACT in response to exogenously added IL-1 (see Example 6). When the mixed cultures of astrocytes and microglial cells are prepared from areas of human brain that are prone to developing mature amyloid pathology, such as the frontal cortex or the hippocampus, the astocytes spontaneously express α$_1$-ACT as the cultured cells reach confluence. Confluence refers to cells in culture which have grown to the extent that there is no remaining space left between the cells. Confirmation that astrocytes are indeed the cells which produce α$_1$-ACT in response to IL-1 is provided by the observation that the same level of α$_1$-ACT production is induced by a given concentration of exogenously added IL-1 when microglial cells are removed from the mixed cultures as in mixed cultures retaining the microglial cells.

The release of α$_1$-ACT from astrocytes in confluent mixed cultures is apparently in response to IL-1 released from the microglial cells. Support for this proposal comes from the observation, discussed above, that the same amount of α$_1$-ACT mRNA is produced in mixed cultures of astrocytes and microglial cells compared with pure astrocytes in response to the same amount of IL-1 (see Example 10). Because there are no significant differences in the number of microglia removed from cortical and cerebellar cultures (see Example 10), it seems likely that the difference between these two cultures resides in the ability of microglial cells from the cortical region to secrete and/or synthesize IL-1. This proposal is consistent with the observation that there are fewer IL-1 positive microglial cells in normal cortex than in Alzheimer's brain cortex (Griffin, et al., *Proc. Natl. Acad. Sci. USA* 86:7611 (1989)). Support for this proposal is also provided by the observation that mixed cultures of astrocytes and microglial cells from non-susceptible areas of the brain, such as the cerebellum or the brain stem, must be induced to express α$_1$-ACT by addition of exogenous IL-1 (see Example 8). In addition, fewer IL-1 positive cells are found in the cerebellum than the cortex of Alzheimer's brain (see Example 11).

This regional specificity of IL-1 release, the differential responses of these regions to IL-1, along with the other results presented herein, support the conclusion that the over-expression and release of α$_1$-ACT and ApoE4 are factors in accelerating the formation of mature amyloid filament deposits.

The release of α$_1$-ACT from astrocytes originating from susceptible areas of the brain suggests that the deposition of mature amyloid plaques and the formation of neurotoxic Aβ filaments can be suppressed by interfering with the response of these astrocytes to IL-1. Support for the proposal is provided by the discovery that antibodies which block the IL-1 receptor prevent the spontaneous production of α$_1$-ACT in confluent mixed cultures of astrocytes and microglial cells prepared from areas of the human brain that are prone to developing mature amyloid pathology (see Example 9). These results provide the basis for an effective method of screening for prospective drugs to treat Alzheimer's disease; such an assay determines whether contacting astrocytes with IL-1 and in the presence and in the absence (control) of a compound being screened results in less release of α$_1$-ACT from the astrocytes in the absence of the compound than in its presence. Alternatively, the assay determines whether confluent astrocytes and microglial cells which have been isolated from areas of the brain that are susceptible to developing mature amyloid plaques release less α$_1$-ACT in the presence of a compound being screened than in the absence of the compound. The results discussed above also suggest that the formation of neurotoxic Aβ filaments and deposition of mature amyloid plaques can be suppressed by interfering with the ability of microglia in susceptible areas of the brain, e.g. the cortex, to release and/or produce IL-1. The assay can also determine whether contacting the cell mixture with the compound being screened results in a decrease in IL-1 release from the microglial cells.

The release of interleukin 1 from microglial cells in the brain should lead to altered levels in interleukin in biological fluids outside of the brain, e.g. the cerebrospinal fluid and blood. Determining altered levels of interleukin 1 in these biological fluids thus provide a method of detecting Alzheimer's disease in an individual. It is also a method of diagnosing Alzheimer's disease before the onset of symptoms normally associated with the disease.

The present invention relates to methods of identifying compounds which inhibit the processes involved in the progression of Alzheimer's disease. These processes include the formation of Aβ filaments, the enhanced ability of astrocytes from susceptible areas of the brain to release $\alpha_1$-ACT in response to IL-1 and neuronal cell death resulting from the formation of Aβ filaments. The present invention further relates to methods of inhibiting these processes.

One embodiment of the present invention is a method of screening for compounds which inhibit the formation of Aβ filaments. "Compound" in the present invention refers to small organic or inorganic molecules, oligopeptides or peptides, as well as to molecules designed to mimic the structure or function of peptides or oligopeptides. For example, specific RNA molecules can be developed and screened for activity against enzymes. The method comprises contacting the compound being screened for its ability to inhibit the formation of Aβ filaments with Aβ and one or more amyloid associated proteins which promote the formation of Aβ filaments, under conditions suitable for the formation of Aβ filaments. This mixture is referred to as the test sample. Amyloid associated proteins which promote the formation of Aβ filaments include $\alpha_1$-ACT, ApoE2, ApoE3 and ApoE4. The method further comprises determining the amount of Aβ filaments formed in the test sample and comparing the amount formed to a suitable control. The control sample is run identically to the test sample, except that the control is run in the absence of the compound being tested for its ability to inhibit the formation of Aβ filaments. The control can be run simultaneously with the test sample. Alternatively, the control is run prior to or after the test sample, in which case it is used as pre-determined standard. The formation of a lesser amount of Aβ filaments in the presence of the compound being screened compared with the amount formed in the control indicates that the compound being screened inhibits the formation of Aβ filaments. Determining the extent to which Aβ filaments form in the test sample and in the control sample can be carried out by methods known to those skilled in the art, including electron microscopy. Electron microscopy can be used to quantitatively determine the amount of Aβ filament formed. Alternatively, electron microscopy can be used to approximate the amount of Aβ filaments formed, for example by visual approximation, or to determine the presence or absence of Aβ filaments in the test sample. Light scattering can also be used to determine the degree of filament formation. Differential precipitation or filtration of the reaction in which Aβ is used having a radioactive label, fluorescent label, a chromogenic label or an enzyme label that can be detected by its activity are also techniques which can be employed to measure Aβ filament formation.

Another embodiment of the present invention is a method of identifying an inhibitor of the formation of Aβ filaments or a compound which suppresses neurotoxic filament formation by identifying a compound which binds $\alpha_1$-ACT (or ApoE4) such that $\alpha_1$-ACT (or ApoE4) no longer binds Aβ. An inhibitor of the formation of Aβ filament formation or a suppressor of Aβ filament neurotoxicity can be identified by combining $\alpha_1$-ACT (e.g. in solution or bound to solid support), chymotrypsin, a chymotrypsin substrate (i.e. a peptide which can be cleaved by chymotrypsin) and the compound being assessed to give a test combination. The test combination is subjected to conditions suitable for cleavage of the substrate. The amount of cleaved substrate is then assessed by methods known in the art (e.g. by use of a chromogenic substrate, a radiolabeled substrate or a biotinylated substrate) and compared to a suitable control. A suitable control is the test combination without the compound being assessed, subjected to the conditions suitable for cleavage of the substrate. If the cleavage of the chymotrypsin substrate occurs to a greater extent in the test combination than in the control, the compound being assessed binds $\alpha_1$-ACT, thereby inhibiting the formation of Aβ filaments and suppressing the neurotoxicity of Aβ filaments.

Another embodiment of the present invention is a method of screening for a compound which suppresses neuronal cell death in Alzheimer's patients. This method comprises contacting a first culture of neuron or neuron-like cells with Aβ, one or more amyloid associated proteins which promote the formation of neurotoxic Aβ filaments, and a compound being screened for its ability to suppress neuronal cell death in an Alzheimer's patient. The first culture is contacted with these components under conditions suitable for neuronal cell survival. The degree of cell death is assessed and compared to a suitable control. A suitable control is a second culture of the neuron-like cells, Aβ and the one or more amyloid associated proteins which promote the formation of neurotoxic Aβ filaments. The second culture of neuron-like cells is contacted with these components under conditions suitable for cell survival. These conditions are identical with the conditions used in the screening being performed with the first culture, except that the compound being screened for its ability to inhibit Gneuronal cell death is not present in the control. The control can be run simultaneously with the screening being performed with the first culture. Alternatively, the control is run prior to or after the screening being performed with the first culture, in which case it is a pre-determined standard. Less cell death in the first culture as compared with cell death in the control is indicative of a compound which can suppress neuronal cell death in the brain of an Alzheimer patient. The degree of cell death or cell toxicity can be determined by a number of methods known to those skilled in the art, including assaying apoptosis by nucleic acid degradation using standard commercially available kits, an MTT release assay, visual inspection in the light microscope and Trypan blue exclusion. The degree of cell death can be determined quantitatively, approximated or determined by the presence or absence of neuronal cell death.

Neuron cells or neuron-like cells may be used in the method of screening for a compound which suppresses neuronal cell death in Alzheimer's patients include neurons from human or animal brains. Preferred neuronal cells are human cortical neurons. As defined herein, neuron-like cells are those cells which have one or more characteristics of neuron cells, including action potentials, processes and the ability to release neurotransmitters. Preferred neuron-like cells are those that have processes. Suitable neuron-like cells include continuously growing cell lines that have been differentiated into neuron-like cells with nerve growth factor (NGF) or a differentiation factor such as retinoic acid can be used. Suitable continuously growing cell lines include neuroblastoma cells, cells formed by a fusion of neuroblastoma cells and neurons and P19 embryo carcinoma cells. A preferred continuous growing cell line is the PC-12 cell line.

A further embodiment of the present invention is a method of screening for compounds which suppress the formation of neurotoxic Aβ filaments. This method comprises contacting a first culture of astrocytes cells with IL-1 and a compound being screened for its ability to suppress the formation of neurotoxic Aβ filaments. Alternatively, the first culture can be a mixed culture which includes astrocytes and microglial cells which have been isolated from areas of the brain which are prone to developing mature amyloid pathology and which have reached confluence. Areas of the brain prone to developing mature amyloid pathology include the hippocampus, the frontal cortex and the amygdala. Reaching confluence refers to astrocytes and microglial cells in culture which have grown to the point where there is no further space for growth left between the cells. Because microglial cells in these confluent mixed cultures spontaneously produce IL-1, there is no need to add exogenous IL-1 if the mixed culture is used in the assay. The amount of $\alpha_1$-ACT produced in the first culture is determined and compared to the amount $\alpha_1$-ACT produced in a second culture of astrocytes and microglial cells that serves as a control culture. Alternatively, the amount of IL-1 produced in the first culture by the microglial cells in determined and compared to the amount of IL-1 produced by the microglial cells in the second culture. The microglial cells may also be replaced with other IL-1 secreting cells. The control is performed identically to the first culture, except that the culture is not contacted with the compound or molecule being screened for its ability to inhibit the formation of neurotoxic Aβ filaments. The production of less $\alpha_1$-ACT or less IL-1 in the first culture compared with the second culture is indicative that the compound being screened suppresses the amount of neurotoxic Aβ filament formation in the brains of Alzheimer's patients. The amount of $\alpha_1$-ACT or IL-1 produced in the control can be assessed simultaneously with the screening of a compound in the first test culture. Alternatively, the control can be run prior to or after screening being performed with the first test culture, and they serve as a predetermined control.

The amount of $\alpha_1$-ACT produced can be assessed by methods known to those skilled in the art, for example by a Northern blot analysis of the total RNA produced by the astrocytes using autoradiography with radioactive $\alpha_1$-ACT cDNA as a probe. The $\alpha_1$-ACT RNA hybridizes with the $\alpha_1$-ACT cDNA, which allows the amount of $\alpha_1$-ACT RNA present to be determined by exposing the blot to photographic film and then determining the intensity of the spot left on the film by the radioactive probe. The amount of $\alpha_1$-ACT mRNA corresponds to the amount of $\alpha_1$-ACT that is being expressed by the astrocytes. The intensity of the spot can be determined quantitatively by densitometer analysis or phosphorimager analysis of the original Northern blot, approximated, or determined by the presence or absence of the spot. Alternatively, methods such as "dot blots" on nitrocellulose or nylon membranes or the like or ELISA assays using antibodies against $\alpha_1$-ACT protein can be used. The binding of a labeled substrate for $\alpha_1$-ACT such as chymotrypsin or a small peptide which should bind $\alpha_1$-ACT, such as Aβ or other peptides resembling the active site of serine proteases, can also be used in ELISA-type assays for measuring the amount of $\alpha_1$-ACT protein generated by the astrocytes.

The amount of IL-1 produced can be analyzed by methods known in the art, including an assay employing a D10 cell line. These are cells which only grow in the presence of IL-1. D10 cells in a test sample are contacted with an aliquot from a culture being tested for the presence of IL-1. Radiolabeled thymidine is added. A control sample is run identically to the test sample, except that an aliquot from the culture being tested is not added. After a suitable period of time, the DNA from both samples are isolated and the amount of radioactivity present is determined. Less radioactivity in the test sample than in the control sample is indicative that less IL-1 is produced in the culture being tested.

Another embodiment of the present invention is a method of suppressing the formation of neurotoxic Aβ filaments. The method consists of contacting Aβ and one or more amyloid associated proteins which promote the formation of Aβ filaments with a compound that inhibits the formation of a complex between Aβ and the one or more amyloid associated proteins. Compounds which inhibit the formation of a complex between Aβ and $\alpha_1$-ACT include peptides comprising $A\beta_{1-12}$ and $A\beta_{1-28}$. They also include oligopeptides with a sufficient number of amino acid residues 1–12 of Aβ that the oligopeptide binds $\alpha_1$-antichymotrypsin. The oligopeptide can include amino acid residues which, in the Aβ peptide are contiguous or are non-contiguous. It can include $A\beta_{1-11}$, $A\beta_{1-10}$, $A\beta_{1-9}$, $A\beta_{2-11}$, $A\beta_{2-10}$ and $A\beta_{2-9}$. The amino acid residues can be naturally occurring or modified, e.g. the oligopeptide can be synthetic. Such compounds further include those peptides which mimic the binding site of serine proteases. Peptides which mimic the binding site of serine proteases will typically have an Asp-Ser-Gly tripeptide, a conserved portion of the serine protease binding site, or its equivalent as part of the amino acid sequence. Potter et al., *Ann. of the N.Y. Acad. Sci.* 674:161 (1992). Compounds which inhibit the formation of complexes between Aβ and $\alpha_1$-ACT also include synthetic peptides or compounds sufficiently homologous to the binding site of $\alpha_1$-ACT that they bind Aβ. Compounds which inhibit the formation of a complex between Aβ and ApoE4 include peptides comprising $A\beta_{1-20}$ and $A\beta_{12-28}$ and oligopeptides comprising a sufficient number of amino acid residues 1–12 or 12–28 of Aβ that the oligopeptide binds $\alpha_1$-antichymotrypsin or Apolipoprotein E4, respectively. Also included are synthetic peptides or compounds sufficiently homologous to ApoE2 that they disrupt the interaction between Aβ and ApoE4.

A further embodiment of the present invention also includes $A\beta_{1-28}$ and $A\beta_{12-28}$ and peptides sufficiently homologous to $A\beta_{1-28}$ and $A\beta_{12-28}$ that they inhibit the formation of a complex between ApoE4 and Aβ. Such peptides include oligopeptides comprising a sufficient number of amino acid residues 12–28 of Aβ that the oligopeptide binds Apolipoprotein E4. The oligopeptide can include residues which, in the Aβ, are contiguous or non-contiguous. The amino acid residues can be naturally occurring or modified, e.g. the oligopeptide can be synthetic. ApoE4 appears to bind with $A\beta_{12-28}$, which form a β-pleated sheet (Strittmatter et al., *Proc. Natl. Acad. Sci., USA* 90:8098 (1993)). The structural requirements of a β-pleated sheet are well known in the art. Consequently, the skilled artisan is able to choose variations in the amino acid sequence which would not alter the ability of the peptide to form a β-pleated sheet and synthesize these peptides by known peptide synthesis methods. Such peptides would be equally effective in binding ApoE4, and would therefore similarly reduce the Aβ filament formation and neuronal cell death by disrupting the interaction between Aβ and ApoE4. Such peptides are the subject of this invention. Synthetic homologues of $A\beta_{12-28}$ which inhibit the formation of a complex between ApoE4 and $A\beta$ can be identified by the methods of screening of the present invention.

Yet another embodiment of the present invention refers to compounds and synthetic peptides sufficiently homologous to ApoE2 that they disrupt the interaction between $A\beta$ and ApoE4.

Yet another embodiment of the present invention is a peptide comprising $A\beta_{1-12}$ and peptides sufficiently homologous to $A\beta_{12}$ that they bind $\alpha_1$-antichymotrypsin and inhibit the formation of a complex between $\alpha_1$-antichymotrypsin and $A\beta$. Included are oligopeptides with a sufficient number of amino acid residues 1–12 of $A\beta$ that the oligopeptide binds $\alpha_1$-antichymotrypsin. The oligopeptide can include amino acid residues which, in the $A\beta$ peptide are contiguous or are non-contiguous. It can include $A\beta_{1-11}$, $A\beta_{1-10}$, $A\beta_{1-9}$, $A\beta_{2-11}$, $A\beta_{2-10}$ and $A\beta_{2-9}$. The amino acid residues can be naturally occurring or modified, e.g. the oligopeptide can be synthetic. Such compounds further include those peptides which mimic the binding site of serine proteases, as described above.

The skilled artisan is also able to modify active peptides by lengthening the peptide, changing the amino acid sequence, derivatizing amino acids within the sequence or including a non-amino acid or non-peptide structural element within the peptide so as optimize desirable properties of the peptide. Such peptides can be prepared by known peptide synthesis techniques. Derivatization can be accomplished by techniques standard in the art of organic chemistry. Desirable properties which can be designed into these synthetic peptides include optimizing its activity (e.g., its ability to interfere with $A\beta$/ApoE4 interaction), solubility, ability to reach the target site in the brain and ability to avoid degradation within the body. Methods of optimizing these and other properties are well known within the art. For example, increasing the ability of the peptide to cross the blood brain barrier and reach the target site can be accomplished by increasing the lipophilicity of the peptide. Alternatively, the peptide can be modified to include a component that is recognized by a receptor on the blood-brain barrier and allows the peptide to be internalized (brought across the blood-brain barrier) and deposited into the neuropil. Optimizing activity, e.g., the binding between ApoE4 and the synthetic peptide can be accomplished, for example, by synthesizing peptide analogues of $A\beta_{12-28}$ and performing competitive binding assays between the synthetic analogue and $A\beta_{12-28}$. Synthetic peptides with improved ability to inhibit the formation of neurotoxic $A\beta$ filaments can be identified, for example, by synthesizing analogs of ApoE2 and comparing the ability of those analogs with the ability of ApoE2 to prevent the formation of $A\beta$ filaments. The process of optimizing activity can be aided by rational based drug design, for example by determining an X-ray crystal structure of a complex between ApoE4 (or ApoE2) and $A\beta_{12-28}$ and identifying the significant interactions between the two molecules. Optimizing the ability of the peptide to avoid degradation within the body can be done by metabolic studies in animals, for example by injecting radioactive analogues of the peptide and following their metabolic fate.

$A\beta_{12-28}$, $A\beta_{1-12}$ and $A\beta_{1-28}$, synthetic homologues of $A\beta_{12-28}$, $A\beta_{1-12}$, $A\beta_{1-28}$ and ApoE2 and oligopeptides comprising a sufficient number of amino acid residues 1–12 or 12–28 of $A\beta$ that the oligopeptide binds $\alpha_1$-antichymotrypsin or Apolipoprotein E4, respectively, can be used in the methods of the present invention of treating an individual with Alzheimer's disease of the present invention. Alternatively, these compounds can be used in the methods of screening of the present invention to find new and more active compounds for treating an individual with Alzheimer's disease. For example, $A\beta_{12-28}$ can be used as a standard in the method of screening for a compound which suppresses neuronal cell death in an individual with Alzheimer's disease. Compounds which are more effective in preventing cell death in this assay than $A\beta_{12-28}$ are potentially more effective therapeutics than $A\beta_{12-28}$ and can be subjected to further testing. These compounds can also be used to find new and more active compounds for preventing the formation of $A\beta$ filaments. For example, ApoE2 can be used as a standard in the method of screening for a compound which inhibits the formation of $A\beta$ filaments. Compounds which are more effective in preventing $A\beta$ filament formation in this assay than ApoE2 are potentially more effective therapeutics than ApoE2 and can be subjected to further testing.

Other compounds which inhibit the formation of $A\beta$ filaments include compounds which inhibit the formation of a complex among $A\beta$, $\alpha_1$-ACT and ApoE4. Such compounds include those compounds which inhibit the formation of $A\beta$/$\alpha_1$-ACT and $A\beta$/ApoE4 complexes.

Another embodiment of the present invention is a method of suppressing neuronal cell death in the brain of an individual with Alzheimer's disease. This method comprises administering to the individual a therapeutically effective dose of a compound which interferes with the interaction between $A\beta$ and a promoting factor such as ApoE4 or $\alpha_1$-ACT. Interfering with this interaction includes, for example, a compound which binds at or near the site on ApoE4 (or $\alpha_1$-ACT) where $A\beta$ binds, thereby blocking $A\beta$ from binding with ApoE4 (or $\alpha_1$-ACT). It is also possible to interfere with this interaction through the use of a compound which binds to ApoE4 (or $\alpha_1$-ACT) and changes the conformation of ApoE4 (or $\alpha_1$-ACT), thereby making it more difficult for $A\beta$ to bind to ApoE4 (or $\alpha_1$-ACT). Suitable compounds which bind ApoE4, thereby preventing ApoE4 and $A\beta$ binding, include a synthetic peptide which comprises amino acid residues $A\beta_{1-28}$ or $A\beta_{12-28}$. Suitable compounds also include oligopeptides comprising a sufficient number of amino acid residues 1–12 or 12–28 of $A\beta$ that the oligopeptide binds $\alpha_1$-antichymotrypsin or Apolipoprotein E4, respectively, as described above. Interfering with the interaction between ApoE4 (or $\alpha_1$-ACT) and $A\beta$ also includes a compound which binds at or near the site where ApoE4 (or $\alpha_1$-ACT) binds to $A\beta$, or at a site which changes the conformation of $A\beta$, thereby inhibiting ApoE4 (or $\alpha_1$-ACT) from binding to $A\beta$.

Yet another embodiment of the present invention is a method of suppressing the formation of neurotoxic $A\beta$ filaments. In this embodiment, astrocytes and microglia cells from areas of the brain susceptible to developing mature amyloid pathology are contacted with a compound which inhibits the expression of $\alpha_1$-ACT by astrocytes. Inhibiting the expression of $\alpha_1$-ACT by astrocytes, as defined herein, refers to inhibiting the transcription of the $\alpha_1$-ACT gene, preventing the mRNA derived therefrom from being transported out of the nucleus or being translated, or preventing the transport of $\alpha_1$-ACT out of the cytoplasm of astrocytes.

Inhibiting the expression of the $\alpha_1$-ACT gene also refers to blocking the biochemical pathway by which IL-1 communicates with the nucleus of the astrocytes, for example by blocking an IL-1 receptor on the cell surface or reducing the levels of IL-1 in areas of the brain susceptible to forming amyloid plaques. One way of interfering with the biochemical pathway by which IL-1 communicates with the nucleus is by means of monoclonal antibodies which block the IL-1 receptor.

Monoclonal antibodies which block the IL-1 receptor are prepared by immunizing a mouse or other suitable animal with IL-1 receptor protein. These proteins, preferably isolated from astrocytes which may show different receptors than cells outside the nervous system, are used to immunize mice by standard procedures. Following several booster injections of the immunogen and analysis of the ability of the recipient mouse to express antibodies to the IL-1 receptor, the animals are sacrificed, the spleens are harvested and disaggregated into individual cells, which include B lymphocytes. These cells are then fused to a hybridoma partner to immortalize them, and the fusion products plated in appropriate medium that will allow only the fused cells to grow into individual clones. Each clone will express a different antibody, and the collection is screened for those clones expressing antibodies to the IL-1 receptor. Many of these antibodies will bind to the receptor but have no effect on its function. A few will block the function of the IL-1 receptor, which can be assayed by their ability to prevent the D10 cell line from responding to IL-1, or preferably screened by their ability to prevent purified human astrocytes from expressing antichymotrypsin in response to added recombinant IL-1. Cloned cells expressing the blocking antibodies to the IL-1 receptor are then harvested, grown into large cultures, and used to prepare large amounts of the blocking antibody. This blocking antibody may be used for other assays. The antibody may also be used as therapy for Alzheimer's disease. Specifically, the antibody should prevent the IL-1 directed acute phase response in the brain and the expression of ACT in astrocytes. Thus there will be less promotion of amyloid filament formation and less neuronal cell death. Alternatively, the genes for the heavy chain and light chain components of the blocking antibody may be isolated by standard recombinant DNA technology from the mouse cells expressing the antibody. Portions of this gene that code for the IL-1 binding area of the antibody may be subcloned and placed in the contexts of the appropriate light or heavy chain human immunoglobin genes. The composite genes can then be placed into an appropriate cell line for large scale expression of human blocking antibodies against the human IL-1 receptor. These antibodies would be preferable therapeutic agents inasmuch as they will contain only minimal, non-immunogenic regions of the original mouse antibody, and will therefore not be recognized and rejected by the human immune system.

Yet another embodiment of the present invention is a a method of detecting Alzheimer's disease in an individual. The method comprises detecting the level of interleukin 1 in the cerebrospinal fluid of the individual, wherein an altered level of interleukin 1 in the cerebrospinal fluid of the individual is indicative of Alzheimer's Disease in the individual. An "altered level of interleukin 1" means that amount of interleukin 1 found in a quantity of cerebrospinal fluid of the individual being assessed is quantitatively different (e.g. greater) than what is found in a suitable control, i.e. an individual or population of individuals who do not have Alzheimer's disease.

Cerebrospinal fluid can be drawn from an individual by methods known in the art. Interleukin 1 levels can be also be measured by methods known in the art, for example by exposing the spinal fluid to radiolabeled antibodies specific for interleukin 1 and then exposing the resulting solution to antibodies to a solid support which are specific for the radiolabeled antibodies. The amount of radioactivity bound to solid support is indicative of the amount of interleukin 1 in the sample.

Yet another embodiment of the present invention refers to a composition comprising $A\beta$ and one or more promoting factors. Preferred promoting factors include ApoE4 and $\alpha_1$-ACT. These compositions are prepared by mixing $A\beta$ peptide and the promoting factor(s) under conditions suitable for the formation of neurotoxic $A\beta$ filaments. Suitable conditions include molar ratios of promoting factor to $A\beta$, pH, ionic strengths and zinc ion concentrations which promote $A\beta$ filament formation. Molar ratios of $A\beta$ to promoting factor can range from about 1:1 to about 400:1; in one embodiment, it is 200:1 and in another is 4:1. pH can range from about 6 to about 8; typically pH 7.0 is used. Ionic strength can range about 1 $\mu$M to about 0.150M, but 10 $\mu$M is preferred. Zinc ion concentration can range from 0 to about 100 $\mu$M, but 25 mM is preferred. Glycine may optionally be added at concentrations from about 0 to about 1.0 mM. Specific conditions are described in Examples 1, 2 and 4. These novel compositions are useful in creating valuable research tools, for example antibodies against a composition known to result in the neuronal cell death associated with Alzheimer's Disease. The novel compositions of the present invention can be used to create such antibodies by immunizing an animal with these compositions and then isolating the resulting antibodies using methods known to those skilled in the art. These novel compositions are also useful for animal studies, for example by implanting the novel compositions into the brains of animal models to determine under what conditions the symptoms of Alzheimer's disease can be induced and then alleviated. Such studies are particularly useful when performed with an additional experiment, namely simultaneously implanting in the brain of a second animal a composition resulting from admixing $A\beta$ peptide, one or more promoting factors, and a compound which suppresses the formation of neurotoxic $A\beta$ filaments in vitro. Less severe symptoms of Alzheimer's disease in the second animal compared with the first animal indicates that the compound can similarly suppress the formation of neurotoxic $A\beta$ filaments in vivo.

The methods of suppressing the formation of neurotoxic $A\beta$ filaments and neuronal cell death have other uses when performed in vitro. For example, this method can be used to determine which interactions between $A\beta$ and the promoting factor are required for formation of a complex which is neurotoxic. In this method, the region(s) of $A\beta$ and the region(s) of the promoting factor which interact and result in neurotoxic filament formation are identified. The interactions which are disrupted by the presence of the compound which suppresses the formation of neurotoxic filaments are also identified. This determination can be made by techniques known to those skilled in the art, for example by X-ray crystallographic or NMR spectroscopic analysis of the complexes formed by $A\beta$ peptide and the promoting factor both in the presence and in the absence of the compound which suppresses the formation of neurotoxic filaments. This determination will facilitate the design and discovery of other agents which can be used to treat Alzheimer's disease.

The methods of the present invention can also be used to therapeutically treat an individual with Alzheimer's disease, i.e. to suppress the formation of neurotoxic $A\beta$ filaments in the brain of an Alzheimer patient or slow neuronal cell death in an Alzheimer patient. Treating an individual with Alzheimer's disease by one of the methods of the present invention comprises administering a compound which is capable of suppressing the formation of neurotoxic filaments or slowing neuronal cell death to the individual so that a therapeutically effective amount of the compound contacts the requisite proteins and cells in the brain of the individual.

These methods can also be used to treat an individual diagnosed with Alzheimer's disease before the onset of symptoms characteristic of the disease (e.g., loss of memory), thereby slowing the onset of these symptoms. An individual can be diagnosed as having Alzheimer's disease before the onset of symptoms characteristic of Alzheimer's disease, for example, by methods disclosed in U.S. patent application, Ser. No. 08/109,746, and U.S. Pat. No. 5,297,562, the teachings of which are hereby expressly incorporated into this application. The compounds are administered, using known methods, including directly into the brain or into the ventricles of the brain through slow release from microcarriers, gels or chambers containing cells that are genetically engineered to produce the compound being administered. The compounds can be modified in a number of ways, as discussed above, to allow them to cross the blood-brain barrier, making it possible to administer them orally, or by parenteral routes (e.g., intramuscular, intravenous or subcutaneous). The form in which the compounds are administered will be determined by the route of administration. Such forms include, but are not limited to, capsular and tablet formulations (for oral administration), liquid formulations (for oral, intravenous, intramuscular or subcutaneous administration) and slow releasing microcarriers, gels and chambers containing genetically engineered cells that produce the compound (for administration intramuscularly, intravenously or into the brain ventricles). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions. The specific dosage level of active ingredient will depend upon a number of factors, including biological activity of the particular preparation and age, body weight, sex and general health of the individual being treated. These compounds can also be administered to an individual with Alzheimer's disease in combination with other known treatments.

Other proteins are known to be associated with mature amyloid plaques found in the brains of Alzheimer's patients. Such proteins include amyloid P component, heparin sulfate proteoglycan, complement proteins and laminin protein (Eikelenboom and Stam, *Acta Neuropathol.* 57:239 (1982), Coria et al., *Lab. Invest.* 58:454 (1988) and Snow et al., *Am. J. Pathol.* 133:456 (1988). In light of the discoveries disclosed herein, it is reasonable to assume that some or all of these proteins similarly promote the formation of Ag filaments and result in these filaments being neurotoxic. It is also reasonable to assume that these proteins are over-expressed by certain cells in areas of the brain that are susceptible to forming determined by contacting these proteins with Aβ under conditions disclosed herein and following the rate of formation of filaments by the electron microscopy or light scattering experiments whether any of these proteins are, in fact, promoting factors. It can be readily ascertained whether these proteins are contributors to the neurodegenerative qualities of Aβ filaments by contacting these proteins with Aβ in a culture of human cortical neurons or neuron-like PC-12 cells and determining whether neuronal cell death is increased in comparison with cell death in cultures treated in the same manner but without the amyloid-associated protein being screened. Proteins which are determined to be promoting factors and which enhance neurotoxicity are targets for therapeutic drugs in the treatment of Alzheimer's disease and can be used in assays for identifying such drugs. Such methods of treatment and assays are within the scope of the present invention.

Following a local inflammatory response or an injury, a number of systemic changes occur which, together, are called the acute phase response (Kushner, *Ann. N.Y. Acad. Sci.* 389:39 (1982)). Some of the important manifestations of an acute phase response are fever, increased rate of synthesis of a number of hormones, including glucocorticoids, and a rise in the concentration of a number of plasma proteins, including $\alpha_1$-ACT (Kushner, *Ann. N.Y. Acad. Sci.* 389:39 (1982), Bauer, et al., *J. Biol. Chem.* 97:866 (1983) and (Baumann et al., *J. Immun.*, 139:4122 (1987)). The acute phase response can be induced by a number of purified hormones and/or defined secondary production of less $\alpha_1$-ACT or less IL-1 in the first interleukin 6 (IL-6), glucocorticoid and dexamethasone. Agents which can induce this acute phase response are neurotoxic Aβ filament formation in the brains of Results presented herein show that dexamethasone acts synergistically with IL-1 to increase the expression of $\alpha_1$-ACT in astrocytes. Dexamethasone and other acute phase inducing agents can therefore be used either alone or in conjunction with IL-1 in the methods of screening for a compound which suppresses the formation of neurotoxic β-peptide filaments present in an individual with Alzheimer's disease. These results suggest that other acute phase inducing agents can similarly be used in this method of screening. Which acute phase inducing agents are suitable can be identified by the methods of the present invention, i.e. by determining whether $\alpha_1$-ACT mRNA is over-expressed in subconfluent cultures of astrocytes in the presence of the acute phase inducing agent being assessed.

The invention is further illustrated by the following examples, which are not intended to be limiting in any way.

EXAMPLE 1

The Alzheimer Aβ Peptide Forms Amyloid Filaments in Vitro

Biosynthetic $A\beta_{1-42}$ was incubated at a concentration of 80 μM in 100 μl of 10 μM Tris-HCl; pH 7.0 at 22° C. for 8, 24 and 48 hours. Assembly of Aβ into high molecular weight filamentous structures was monitored by light scattering at 400 nM. Light scattering increases linearly according to the size and number of filaments formed. The results are shown in FIG. 1 and indicate that Aβ peptide spontaneously forms amyloid filaments, starting after about 8 hours of incubation; the rate of formation levels off after about 24 hours.

At 18 hours, filaments were applied to carbon-coated Formvar on 200 mesh copper grids, dried, negatively stained with 3% uranyl acetate and visualized in a JEOL-100CX electron microscope. Many small and a few large filaments were visible in the electron micrograph and are representative of the products of this polymerization reaction.

EXAMPLE 2

Figure 2:
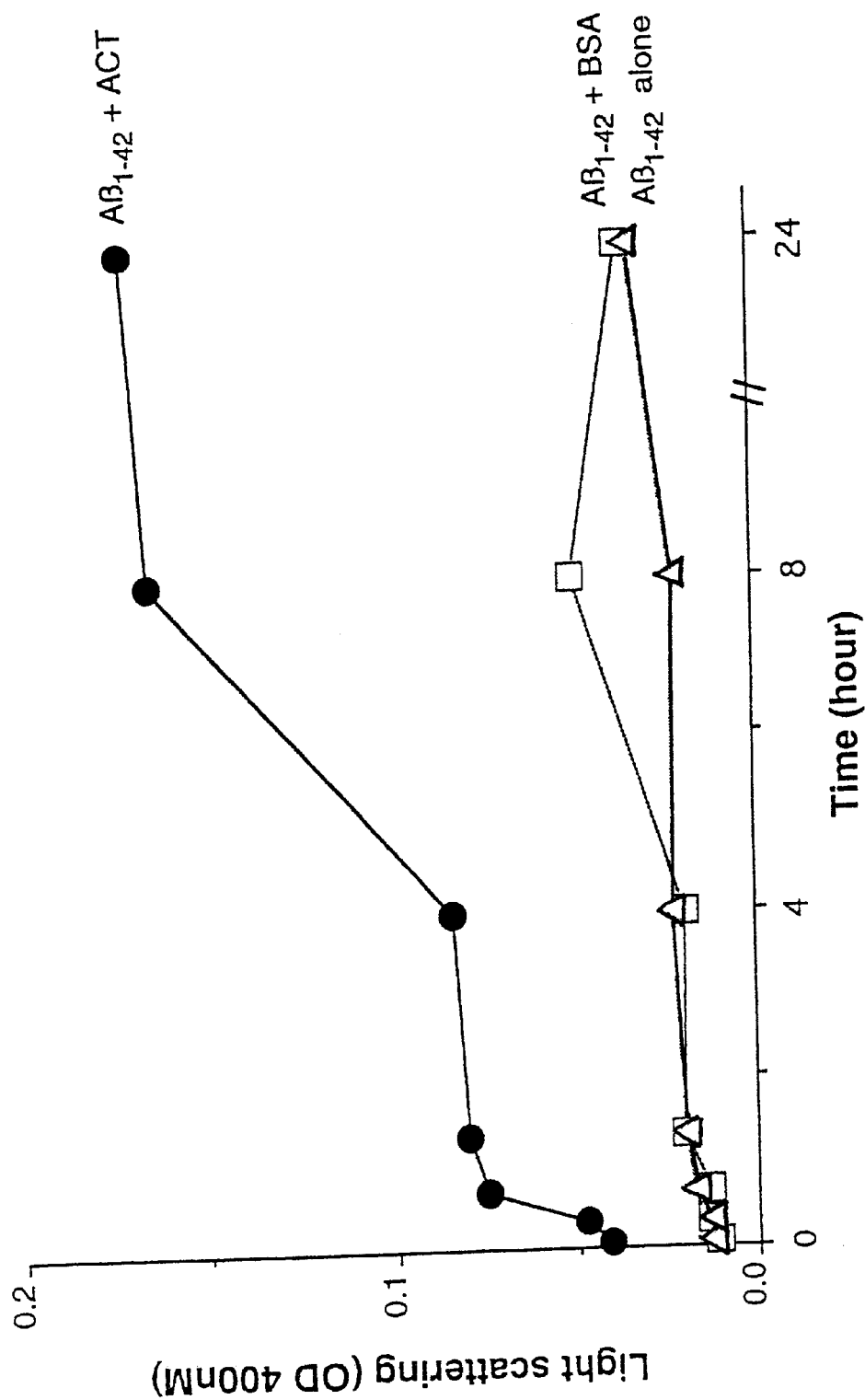
FIG. 2 is a graphic representation of the rate of the formation in vitro of Aβ filaments over time from a mixture Aβ and $\alpha_1$-ACT compared with the rate of formation of the filaments from Aβ alone and from a mixture of Aβ and the protein BSA. The rate of formation is monitored by light scattering.

The Alzheimer Amyloid Associated Protein $\alpha_1$-ACT Promotes the Assembly of Aβ Protein into Filaments The $A\beta_{1-42}$ was incubated, as described in Example 1, in the presence or absence of $\alpha_1$-antichymotrypsin or a control protein (BSA) at a molar ratio of 200:1. Filament assembly was monitored by light scattering. The results are shown in FIG. 2 and indicate that $\alpha_1$-ACT results in the rate of filament formation being enhanced about ten-fold over the controls. Formation of filaments was essentially complete after about 8 hours.

The degree of filament formation was analyzed using electron microscopy. The reaction mixture was diluted with water or buffer. A Formvar-coated copper electron microscope grid was touched briefly to a droplet of the reaction mixture, allowing the filaments to stick to the Formvar plastic film. This procedure was also performed with Formvar which was precoated with carbon prior to the sticking of the filaments to the surface. The filaments were then stained with either a solution of uranyl acetate or sprayed ("shadowed") with a heavy metal such as platinum to allow their visualization. Electron microscopic examination of the reaction product revealed large numbers of long, 6 nM-wide, amyloid-like filaments, and many shorter filaments. $\alpha_1$-ACT promoted filament information at least ten-fold (see also FIG. 3).

EXAMPLE 3

The Amyloid Associated Protein Apolipoprotein E Promotes the Assembly of A$\beta$ Peptide into Filaments The A$\beta_{1-42}$ peptide was incubated in the presence of purified Apolipoproteins E2, E3 and E4 and $\alpha_1$-ACT, ApoAI and ApoAII at a molar ratio of 4:1, as described in Examples 1 and 2. Electron microscopic examination of the reaction products was used to quantitate the amount of A$\beta$ filament formation from the reaction of A$\beta$ with ApoE3, ApoE4 or $\alpha_1$-ACT. Five randomly chosen electron micrographs of each reaction product after 18 hours of incubation as in Examples 1 and 2 were analyzed by counting the number of crossovers that the filaments underwent with each other. This provides a measure of both the number and length of the amyloid filaments per unit area of the grid. The results, shown in FIG. 3, indicated that ApoE4, ApoE2, $\alpha_1$-ACT and ApoE3 all promote the formation of A$\beta$ filaments. However, ApoE4 was about four times more active than ApoE3 or $\alpha_1$-ACT. ApoE2 was the least active of the ApoE proteins, promoting the formation of less than half the quantity of A$\beta$ filaments than were produced in the presence of ApoE3 or $\alpha_1$-ACT. The formation of A$\beta$ filaments was inhibited when ApoE4 was incubated with A$\beta$ in the presence of ApoE2 and equimolar amounts of ApoE4 and ApoE2 were used. Reducing the amount of A$\beta$ filament formed to levels produced by the control protein, BSA (see FIG. 3). ApoA1, ApoAII and BSA were inactive.

EXAMPLE 4

Neurotoxicity of Alzheimer $\beta$-Peptide Filaments Formed in the Presence of Promoting Factors Certain promoters of the assembly of A$\beta$ filaments of amyloid filaments formed in vitro also result in these filaments being neurotoxic. This was determined by using fetal human cortical tissue from 18–22 week gestation were used for this study. The protocol obtaining postmortem fetal tissue complied with all federal guidelines for federal research. The cortical cell culture were prepared as follows. The frontal and temporal lobes were removed from fetal brain. Cells were disassociated in calcium and magnesium free Hank's balanced salt solution containing 0.2% tyrosine for 10 minutes at room temperature, and subsequently disassociated in serum-containing Dulbecco's Modified Eagle Medium (D-MEM) with DNase (0.2 mg/ml) for three times. The cells were plated onto laminin (10 $\mu$g/ml) coated 96-well plate ($10^{-4}$ cell/well) in a neuronbasal medium supplemented with B27 (Gibco), 2 mM glutamine and 1x antibiotic antimycotic solution and kept in a humidified 5% $CO_2$ atmosphere. After 2–3 days in vitro (DIV), non-neuronal cell division was halted by 2 days exposure of $10^{-5}$ cytosine arabinoside and cells were shifted into the plating medium. Subsequent media replacement was carried out on a biweekly schedule.

Figure 3:
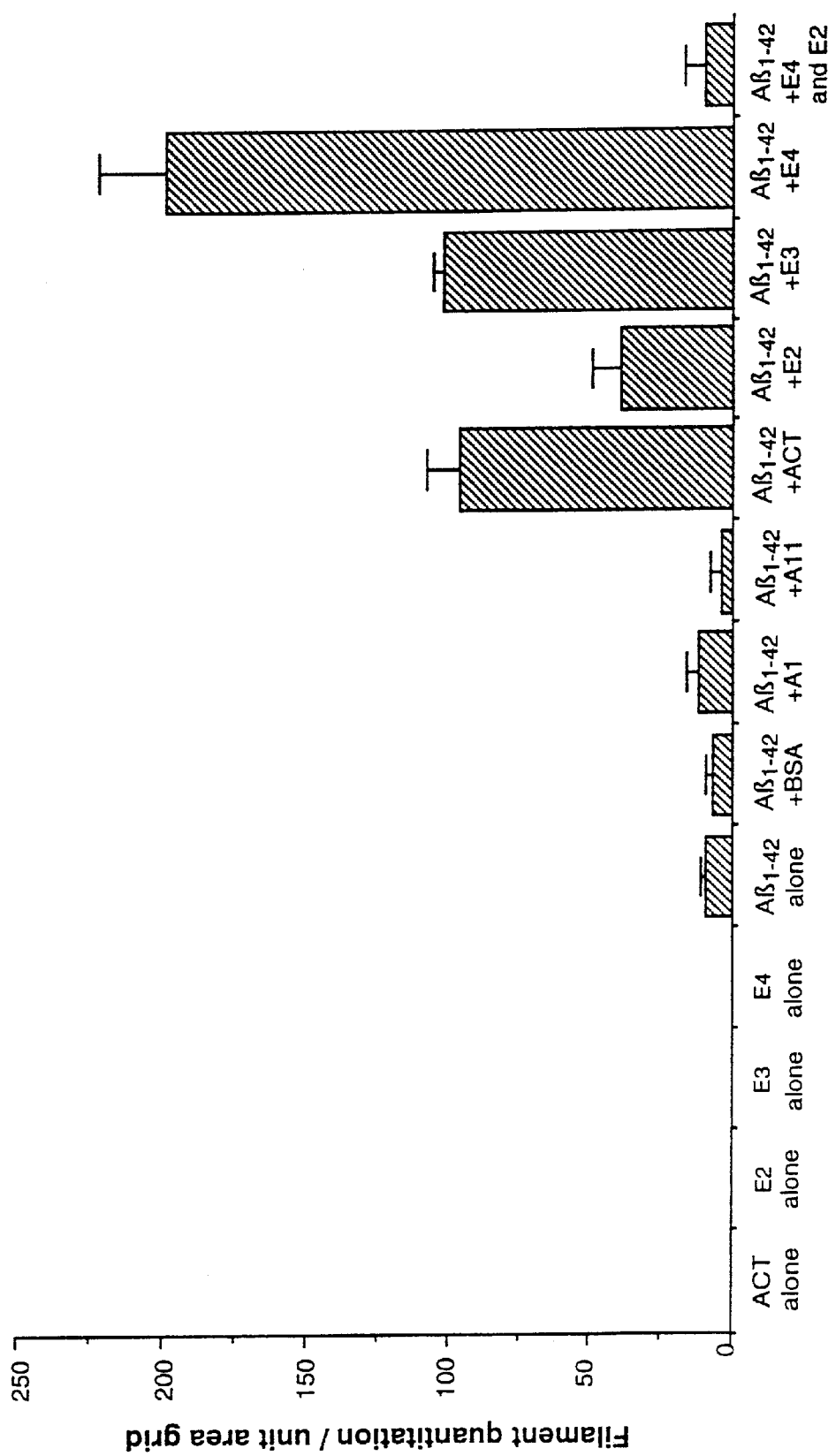
FIG. 3 compares in tabular form the amount of Aβ filaments formed in vitro from the mixture of Aβ and $\alpha_1$-ACT, ApoE2, ApoE3, ApoE4 Apolipoprotein AI (ApoAI) or Apolipoprotein AII (ApoAII). The formation of the filaments was determined by quantitative electron microscopy.

The products of the reactions shown in FIG. 3 were both applied to two or three sister cultured wells on day 12. Cell viability was evaluated by morphological criteria and colorimetric MTT (Tetrazolium) on day 16. MTT 5 mg/ml was dissolved in serum free D-MEM and filtered to sterilize. 25 $\mu$l of the 5 mg/ml solution of MTT was applied to each assayed wells following removal of all culture medium from the plates, and plates were incubated at 37° C. for 3 hours. 100 $\mu$l dimethyl sulfoxide (DMSO) were then added into each well and mixed thoroughly to dissolve the dark crystals. The plates were read on a BT 1000 microreader, using a test wavelength of 550 nm, a reference wavelength of 650 nM. The plates were routinely read within 20 minutes of addition of DMSO.

Figure 4:
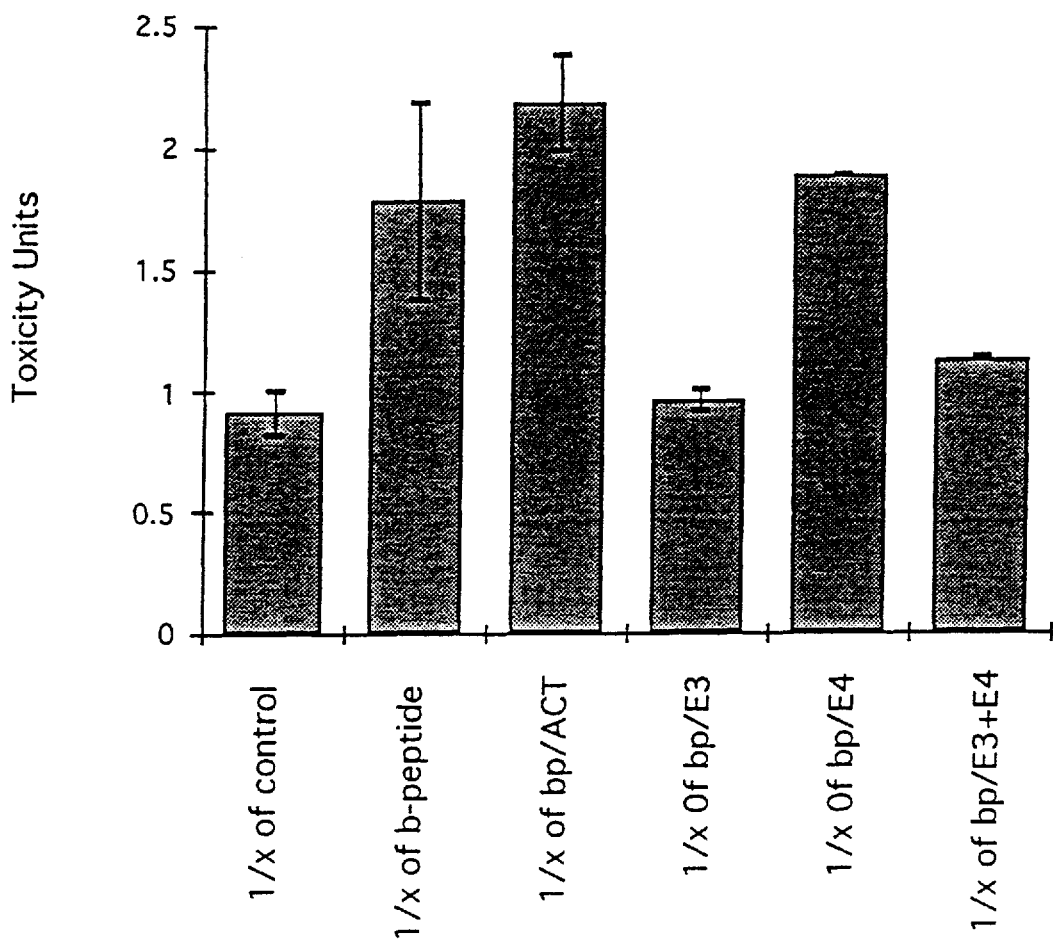
FIG. 4 compares in tabular form the neurotoxicity of Aβ filaments to human cortical neurons formed from the reaction of Aβ and various promoting factors.

The results are shown in FIG. 4. The greatest neurotoxicity was exhibited by the reaction mixtures containing A$\beta$ plus $\alpha_1$-ACT or A$\beta$ plus ApoE4. A$\beta$ alone was also neurotoxic, possibly by reacting first with $\alpha$-ACT-like proteins in the serum used to grow the cells. ApoE3 not only did not promote the development of neurotoxic activity, but reduced the activity of the A$\beta$ peptide itself.

Similar results were also obtained using neuron-like PC-12 cells and neonatal rat cortical neurons as targets for the neurotoxic activity of amyloid filaments. The procedure for performing the assay for neurotoxicity using neuron-like PC-12 cells is the same as described is Example 5 except that the blocking peptides are not added to the assay.

EXAMPLE 5

The Effect of Blocking Peptides on the Neurotoxicity of Alzheimer $\beta$-Peptide Filaments PC-12 cells were grown on normal tissue culture plastic in serum-containing medium. When they reached 75% confluence, they were replated in two sets of 96-well dishes precoated with poly-D-lysine and laminin at $10^6$ cells per well in N2 medium. After two days, NGF at 100 ng/ml was added to each well to induce neurite outgrowth. 1–2 days later, the cells were fed with fresh N2 medium lacking NGF. The reaction mixtures containing $\beta$-protein, $\pm\alpha_1$-antichymotrypsin, Apolipoprotein E, or the various blocking peptides, were added one day later. Reaction mixtures containing $\beta$-protein, $\pm\alpha_1$-antichymotrypsin and the various blocking proteins along with reaction mixtures containing appropriate combinations thereof for controls were added to the first set of dishes. Reaction mixtures containing $\beta$-protein, Apolipoprotein E4 and the various blocking proteins along with reaction mixtures containing appropriate combinations thereof for controls were added to the second set of dishes. After one more day of incubation, the MTT release assay was carried out to measure neurotoxicity.

Figure 5:
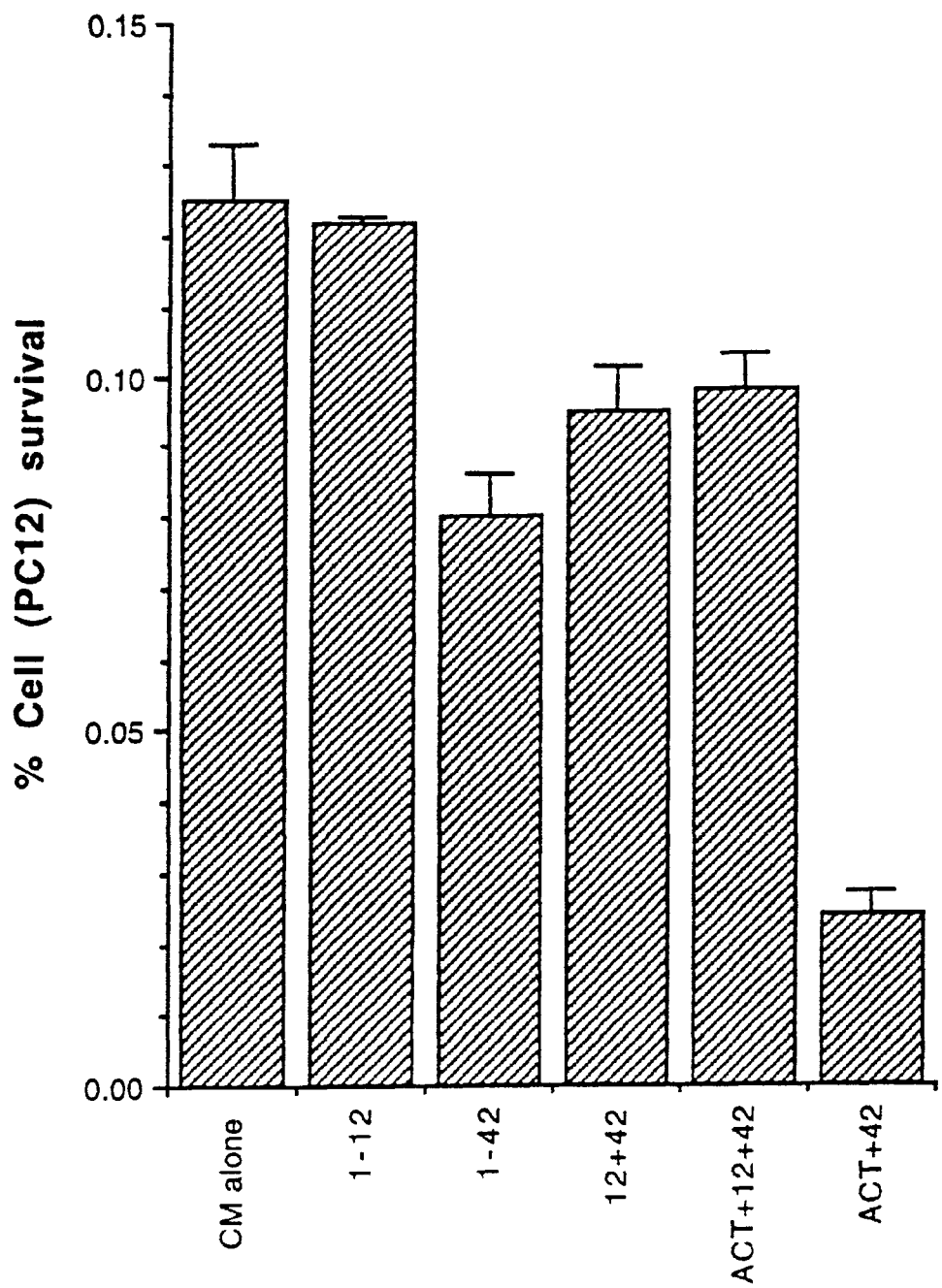
FIG. 5 shows in tabular form the ability of Aβ$_{1-12}$ to suppress the neurotoxicity of the combination of Aβ and $\alpha_1$-ACT towards neuron-like PC-12 cells.

FIG. 5 shows the results of the set of dishes which tested the ability of blocking proteins to suppress the neurotoxicity of $\beta$-protein and $\alpha_1$-antichymotrypsin. Reaction mixtures containing only $\beta$-protein and $\alpha_1$-antichymotrypsin were highly neurotoxic. However, reaction mixtures containing $\beta$-protein, $\alpha_1$-antichymotrypsin and A$\beta_{1-12}$ were about five fold less neurotoxic. In the data shown, standard errors of the means of separate wells in the 96-well dish are presented.

Figure 6:
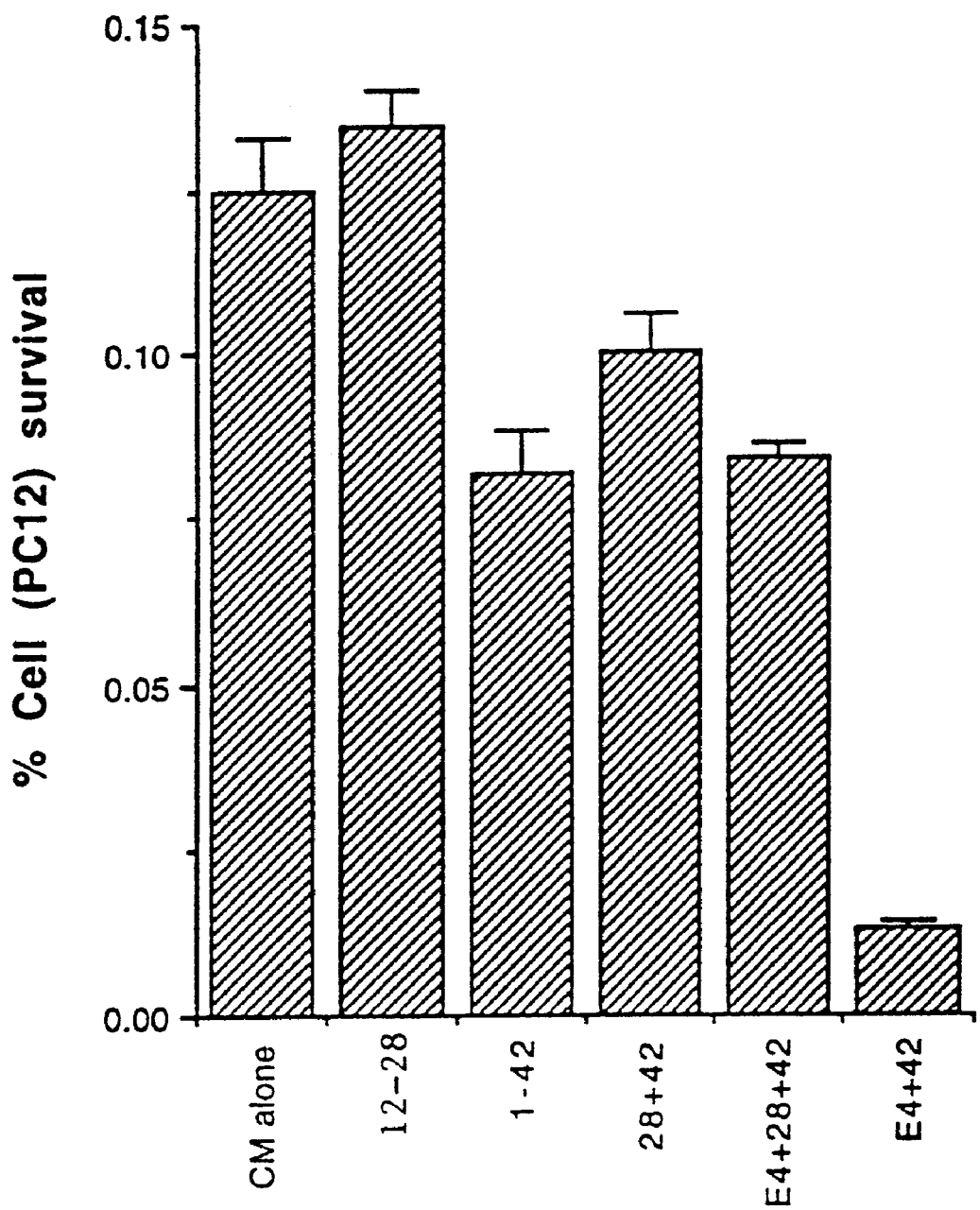
FIG. 6 shows in tabular form the ability of Aβ$_{12-28}$ to suppress the neurotoxicity of the combination of Aβ and ApoE4 towards neuron-like PC-12 cells.

FIG. 6 shows the results of the set of dishes which tested the ability of blocking proteins to suppress the neurotoxicity of $\beta$-protein and Apolipoprotein E4. Reaction mixtures containing only $\beta$-protein and Apolipoprotein E4 were highly neurotoxic. However, reaction mixtures containing β-protein, $\alpha_1$-antichymotrypsin and $A\beta_{12-28}$ were about four to five fold less neurotoxic. In the data shown, standard errors of the means of separate wells in the 96-well dish are presented.

EXAMPLE 6

Determination of the Level of ACT mRNA in Fetal Human Brain

Mixed glial cultures were prepared from portions of human brain of 20-week gestational age from which the meninges, mid, and hind brains had been removed. The tissue was then homogenized and treated with trypsin for minutes at 37° C. A portion of the cells were set aside. Total RNA was isolated from these cells, as described below. The remainder of the partially dissociated cells were suspended in DMEM supplemented with 10% fetal calf serum, 1 mM pyruvate, 100 U/ml streptomycin-amphotericin-penicillin (Sigma, Hybrimax), and 2 mM glutamate. They were triturated 20–25 times and plated on 20 cm plates. The cells were grown in the serum-containing medium until they reached confluence (about 1 week).

After one-two weeks, the majority of neurons had died and detached from the substrate, leaving a confluent monolayer of glial cells. From the morphology of the cells, it appears that most were astrocytes, together with a few microglia. This conclusion was confirmed by immunolabeling of the cells with an antibody to the astrocyte specific protein glial fibrillary acidic protein (GFAP). Cells to be stained for GFAP were grown on poly L-lysine coated coverslips, fixed for 5 minutes in 4% paraformaldehyde at room temperature, then permeabilized with 0.1% Triton X-100 for 1 hour at room temperature. Coverslips with cells were then incubated with a 1/400 dilution of the primary antibody (mouse monoclonal anti-GFAP, Sigma Chemicals) at 4° C. overnight. They were then washed three times for 5 minutes each with PBS. The coverslips were then incubated with the secondary antibody (goat-anti-mouse TRITC conjugate, 1/500 dilution, Sigma Chemicals) for 1 hour at room temperature, washed three times, and mounted on slides for visualization and photography. Visualization was by means of a Zeiss fluorescence photomicroscope. GFAP-positive cells are identified by the fluorescence labeling of their internal filamentous cytoskeleton. The results indicated that >90% of the cells were indeed astrocytes.

One plate of astrocytes was used in each experimental test. Complete medium was first replaced with serum-free N2 medium (high glucose DMEM, 2 mM glutamate, 100 U/ml strep-amp, 1 mM pyruvate, 5 μg/ml insulin, 100 μg/ml transferrin, 100 μM putrescine, 30 nM selenium, and 20 nM progesterone) for 2 hours. The cells were then exposed to the different treatments for 6 hours, except where noted. Following treatment, the cells were harvested, and their RNA isolated for Northern blot analysis.

Total cellular RNA was isolated as described by Chirgwin et al. (1979). Briefly, cells (~10 mg of tissue) were washed with phosphate-buffered saline (PBS) and lysed directly on the culture plate in 1 ml of 4M guanidinium isothiocyanate/ 25 mM sodium citrate, pH 7/0.5% sarcosyl/0.1M 2-mercaptoethanol. The cell lysate was layered on top of 2 ml of 5.7M cesium chloride and centrifuged overnight at 39,000×g. The RNA pellet obtained was resuspended in water, ethanol precipitated, resolubilized in water, and quantitated using spectrophotometry. 3–10 μg samples of RNA were denatured in 2.2M formaldehyde/50% formamide (vol/ vol) and subjected to electrophoresis in a 1% agarose gel containing 2.2M formaldehyde. The gels were stained with ethidium bromide and photographed to verify that each lane contained equal amounts of undegraded RNA. After transfer to nitrocellulose, the RNA was hybridized to [$^{32}$P]-labeled probe. Probes were labeled by priming with random hexamer oligonucleotides in the presence of [$^{32}$P]-dCTP (New England Nuclear). After hybridization, the membranes were washed under conditions of high stringency (0.1×SSC, 55° C.), and exposed to XAR-5 autoradiography film (Kodak). ACT mRNA was undetectable in fetal human brain. However, the autoradiogram indicated a high level of ACT mRNA in serum grown cells that had reached confluence.

EXAMPLE 7

Induction of ACT in Human Astrocytes by IL-1

Mixed glial cultures from human fetal frontal cortex, cerebellum, and brain stem were prepared as described in Example 6, grown to subconfluence in serum-containing medium, then switched to serum-free N2 medium for 2 hours. The cultures were then treated with IL-1 (250 U/ml) and/or dexamethasone (1 μm) for 4 hours, at which time RNA was isolated and subjected to Northern blot analysis with an ACT probe as described in Example 6. IL-1 alone was able to induce ACT expression in cells from three brain areas. There is a synergistic effect of adding dexamethasone together with IL-1. The main difference between the different cultures is that cells prepared from the cortex have a much higher level of endogenous ACT mRNA compared to cells prepared from the cerebellum or brain stem.

EXAMPLE 8

Constitutive Expression of ACT in Cortical but not Cerebellar or Brain Stem Mixed Glial Cultures Cultures of mixed glial cells were prepared as described in Example 6 from human fetal frontal cortex, cerebellum, and brain stem, grown for one to two weeks in serum-containing medium to approximately 80% confluence. The cultures were then switched to N2 medium and allowed to reach confluence over the ensuing twelve hours. RNA was prepared and subjected to Northern blot analysis using an ACT probe as described in Example 6. Cultures prepared from the frontal cortex expressed a high spontaneous level of ACT mRNA, which could not be further induced by the addition of IL-1 and dexamethasone. In contrast, the cultures prepared from the cerebellum or brain stem at various times after they reached confluence continued to express the low level of ACT mRNA seen in subconfluent cultures and were again sensitive to induction by IL-1 and dexamethasone.

EXAMPLE 9

Blockade of Constitutive ACT mRNA Expression in Cortical Mixed Glial Cultures by Antibody to the IL-1 Receptor Human cortical mixed glial cultures were prepared and allowed to reach confluence as described in Examples 6–8, either in the absence or presence of 2.5 μg/ml blocking antibody to the IL-1 receptor. Suitable blocking antibodies to the IL-1 receptor are commercially available from Genzyme Corporation, or can be obtained by immunizing a mouse with IL-1 receptor protein, immortalizing the resulting isolated spleen cells by fusion with a hydridoma partner, and assaying for expressed antibodies which block the IL-1 receptor.

The RNA of the cells of the two cultures was then subjected to Northern blot analysis. Total cellular RNA was isolated as described by Chirgwin et al., *Biochemistry*, 18:5294–5299 (1979). Cells (about 10 mg of tissue) were washed with phosphate-buffered saline (PBS) and lysed directly on the culture plate in 1 ml of 4M guanidinium isothiocyanate/25 mM sodium citrate, pH 7/0.5% sarcosyl/ 0.1M 2-mercaptoethanol. The cell lysate was layered on top of 2 ml of 5.7M cesium chloride and centrifuged overnight at 39,000×g. The RNA pellet obtained was resuspended in water, ethanol precipitated, resolubilized in water, and quantitated using spectrophotometry. 3–10 µg samples of RNA were denatured in 2.2M formaldehyde/50% formamide (vol/ vol) and subjected to electrophoresis in a 1% agarose gel containing 2.2M formaldehyde. The gels were stained with ethidium bromide and photographed to verify that each lane contained equal amounts of undegraded RNA. After transfer to nitrocellulose, the RNA was hybridized to [$^{32}$P]-labeled probe derived from either the human ACT cDNA or the rat ACT homologue, contrapsin, cDNA. Probes were labeled by priming with random hexamer oligonucleotides in the presence of [$^{32}$P]-dCTP (New England Nuclear). After hybridization, the membranes were washed under conditions of high stringency (0.1×SSC, 55° C.), and exposed to XAR-5 autoradiography film (Kodak). Experiments were repeated at least 3 times with similar results.

Northern blot analysis of equal amounts of total RNA isolated from the two cultures indicated that the spontaneous level of ACT mRNA was reduced (at least five-fold) in the presence of the antibody.

EXAMPLE 10

Removal of Microglial Cells from Mixed Cultures and Quantitation of $\alpha_1$-ACT Produced by the Remaining Astrocytes Mixed glial cultures from human fetal front cortex, cerebellum and brain stem were prepared as described in Example 6. Pure astrocytes were prepared by 3 different protocols: (1) Plated cells were incubated with 0.2 mg/ml trypsin for 15 minutes. The supernatant, including non-adherent cells, was discarded. The remaining cells were then washed with HBSS and placed in fresh medium. (2) A standard procedure for obtaining pure astrocyte cultures was carried out according to (Lee, et al., *Lab Invest*, 67:465 (1992)). The subconfluent mixed glial cultures were placed in a rotary shaker at 180 rpm overnight. The supernatant and non-adherent cells were discarded and the remaining cells washed and supplemented with fresh medium. (3) Cultures were treated with 5 mM H-Leu-O-Methyl ester for 18 hours according to (Giullian, *J. Neurosci. Res.*, 18:155 (1987)), after which the adherent cells were washed and fresh medium added. In all three procedures, the cells remaining were >95% astrocytes as determined by morphology. The number of microglia removed from (and therefore present in) the mixed glial cultures was assessed by staining with two macrophage/microglial cell-specific antisera, LN3 and Mac1 (ICN) and were found to be equal from all brain regions ±10–15%.

One plate of mixed glial or pure astrocytes was used in each experimental test. Complete medium was first replaced with serum-free N2 medium (high glucose DMEM, 2 mM glutamate, 100 U/ml strep-amp, 1 mM pyruvate, 5 µg/ml insulin, 100 µg/ml transferrin, 100 µM putrescine, 30 nM selenium, and 20 nM progesterone) for 2 hours. The cells were then exposed to IL-1 (250 U/ml) and/or dexamethasone (1 mm) for 6 hours. Following treatment, the cells were harvested, and their RNA isolated for Northern blot analysis, as described in Example 6. Pure astrocytes showed no difference from mixed glia cultures in the amount of $\alpha_1$-ACT produced in the presence of IL-1 and/or dexamethasone.

EXAMPLE 11

Quantitation of IL-1 Positive Cells from Different Areas of Alzheimer Brain

Immunohistochemistry for IL-1 was performed as described by (Griffin, et al., *Proc Natl. Acad. Sci. USA* 86:7611 (1989)). Briefly, paraffin-fixed sections from the cerebellum and hippocampus regions from Alzheimer Disease and control brain were processed on slides through three changes of xylenes and rehydrated by processing slides through 100%, 95%, and 75% ethanol. Sections were permeabilized in 0.05% Triton X-100 for 10 minutes followed by 0.2 N HCl for 20 minutes. Endogenous peroxidase was blocked by placing sections in 0.6% $H_2O_2$/methanol for 30 minutes. Blocking of sections was performed in 20% goat serum for 30 minutes. Appropriate dilution of the primary antibody (1:20 for anti-human 1L-1α (Ciston), or direct application of monoclonal LN3 (ICN) was then applied to the sections overnight at 4° C. For 1L-1α staining, a PAP procedure was used. 1:50 dilution of goat anti-rabbit (Sigma) IgG was applied to tissue sections for 30 minutes. 1:300 dilution of rabbit peroxidase anti-peroxidase was then applied for 30 minutes to the section. Finally the sections were developed with DAB, counter-stained with hematoxylin, dehydrated and mounted with coverslips. For LN3 staining, the Vector ABC Vectastain kit was used for peroxidase staining, following which sections were counter-stained with hematoxylin, dehydrated and mounted with slipcovers.

The staining, i.e., IL-1 positive glial cells, are not increased to the same extent in the cerebellum as in the hippocampus region of the brain of Alzheimer patients.

EXAMPLE 12

Figure 7:
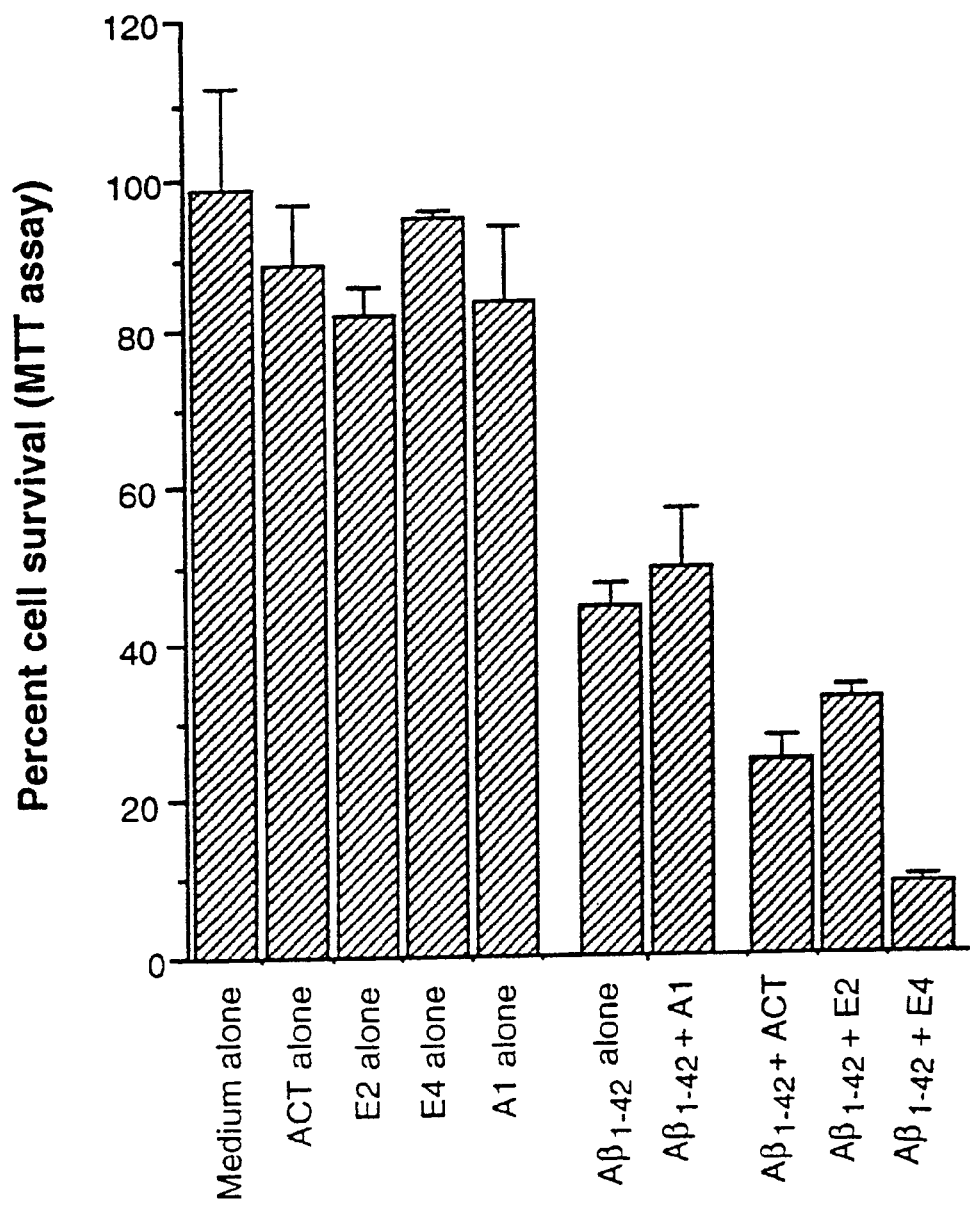
FIG. 7 shows that the pathological chaperones, ACT and apoE4, promote the toxicity of Aβ1–42 in human cortical neurons in culture.
Figure 8A:
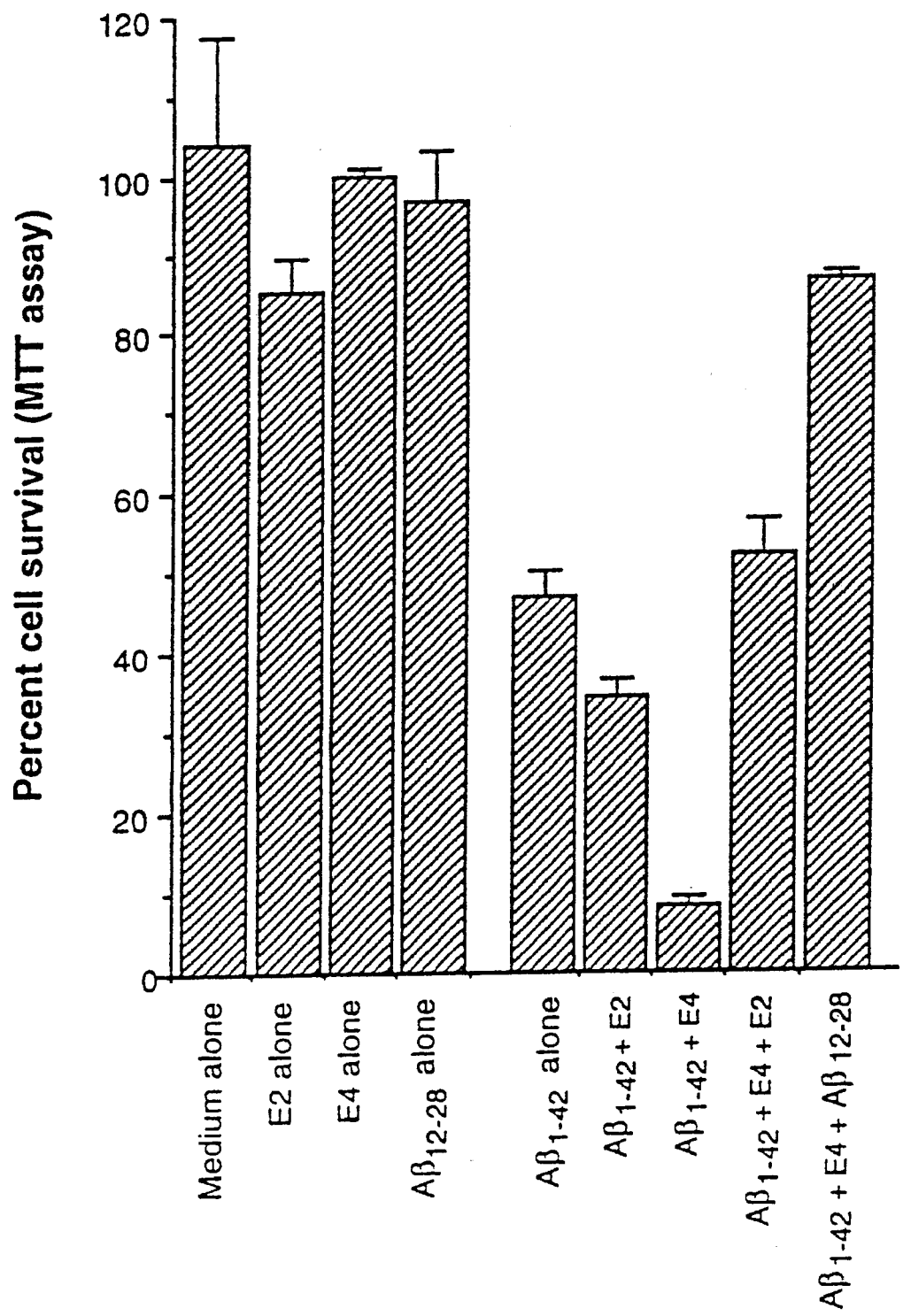
FIGS. 8a and 8b show the neuroprotection effect of anti-pathological chaperons, Aβ-related peptides and apoE2, on human cortical neurons in culture from pathological effects of ApoE4 and ACT respectively.
Figure 8B:
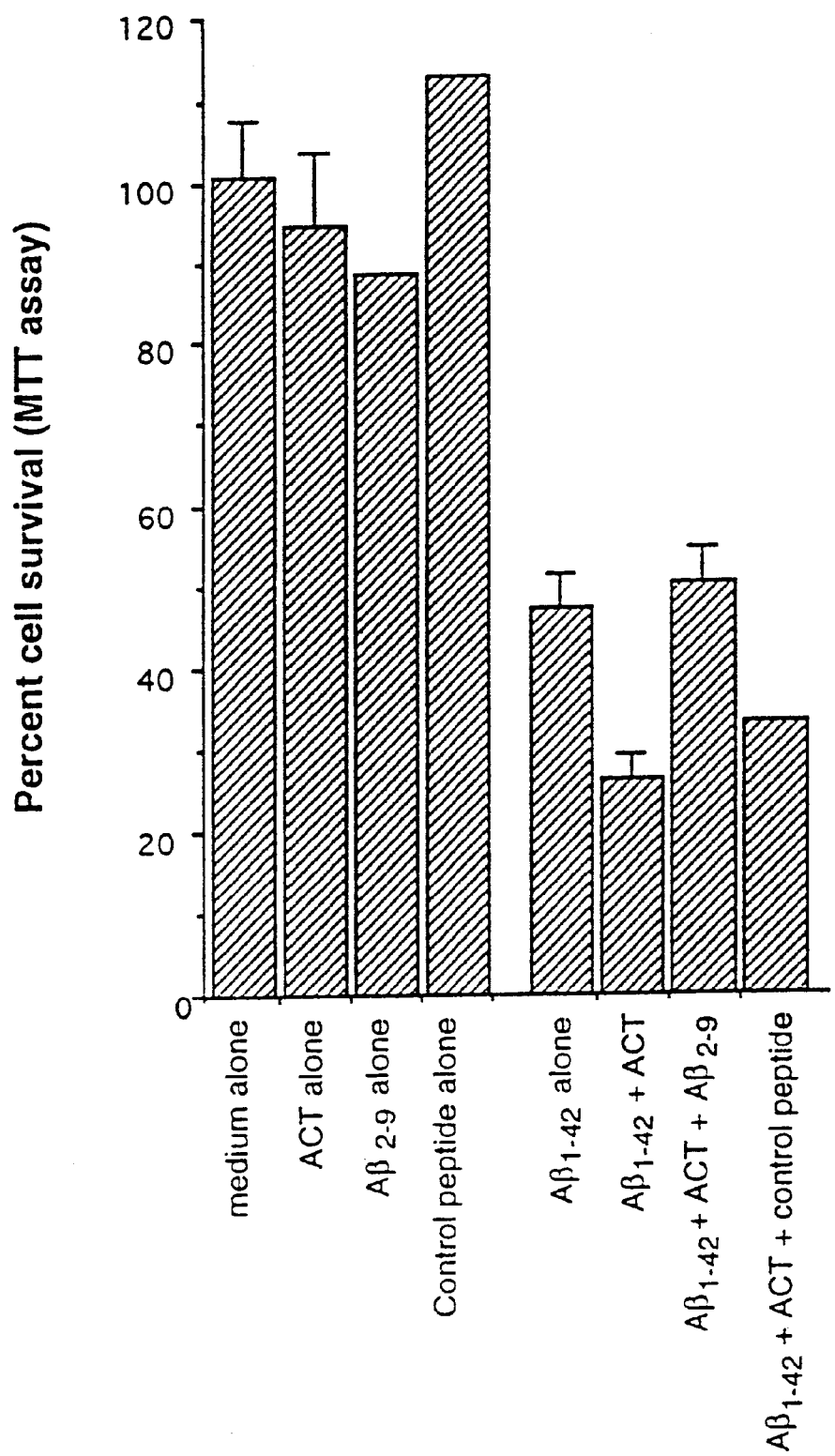
Figure 9A:
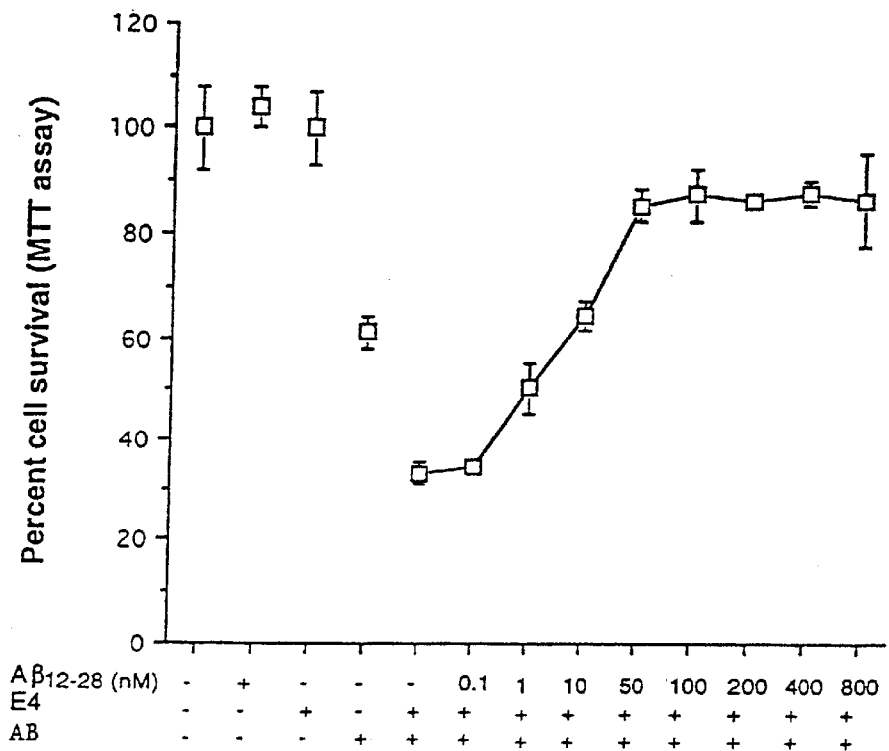
FIG. 9a is a graph showing the effect of the Aβ$_{12-28}$ concentrations on apoE4 neurotoxic Aβ1–42 filaments-promoting activity.
Figure 9B:
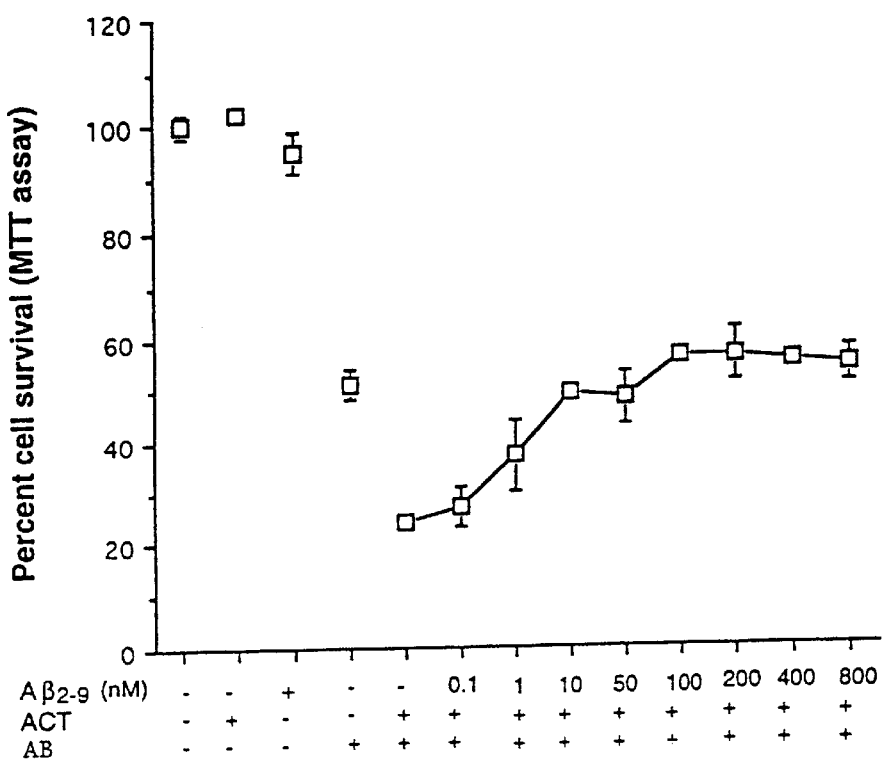
FIG. 9b is a graph showing the effect of the Aβ$_{2-9}$ concentrations on ACT neurotoxic Aβ1–42 filaments-promoting activity.
Figure 9C:
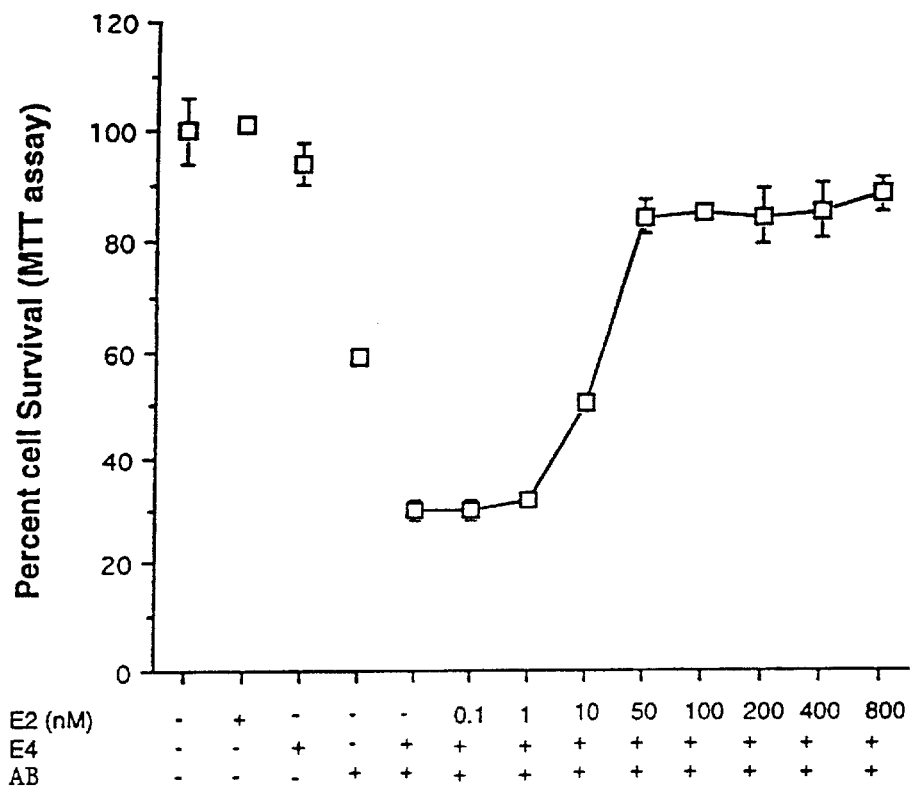
FIG. 9c is a graph showing the effect of the ApoE2 concentrations on ApoE4 neurotoxic Aβ1–42 filaments-promoting activity.

Biosynthetic Aβ1–42 (80 µM) was incubated with ACT (CalBiochem), purified human apoE and individual control protein (0.4 µM) in 100 µl of 10 µM Tris-HCl, pH 7.0 for 48 hours at 22° C. The 12.5 µl of each reaction product was then added to 14 days old primary human cortical neurons in culture. The cell viability was measured by a colorimetric MTT (Sigma) assay on day 4. Data are expressed ±S.E.M. in FIGS. 7–9. ACT and apoE4 induced a 2- and 4-fold increase in neurotoxicity of Aβ1–42, respectively. ApoE2 had a slight effect on Aβ1–42 neurotoxicity. Since Aβ1–42 is prone to self-aggregate into filaments, only aliquots of each preparation of Aβ1–42 devoid of filaments, as judged by electron microscopy, were used for experiments.

Method of cell culture: The cortical neuron cultures were prepared as follows. Frontal lobes of brain were removed from an electively terminated human fetus on gestational age of 18–21 weeks. Cortical cells were dissociated in serum-free medium containing 0.2% trypsin (Sigma) and 25 µg/ml DNase I (Sigma) and plated 4×10$^4$ cells per well (96-well plate, Falcon) precoated with 10 µg/ml laminin (Gibco). The cells were cultured in DMEM (Gibco) supplemented with 10% fetal calf serum (Gibco) and 2 mM glutamine. Cultures were kept at 37° C. in a 7% $CO_2$ atmosphere. After day 4 in vitro, non-neuronal cell division was halted by exposure to 10$^{-5}$M cytosine arabinoside. Culture medium was changed every 3–4 days with complete medium, and changed to neurobasal medium containing B27 (Gibco) one day before addition of each reaction product.

Chemically synthesized Aβ2–9 (0.8 μM) or Aβ12–28 (0.8 μM) was preincubated with ACT (0.4 μM) or apoE (0.4 μM) for 2 hours followed by addition of Aβ1–42 (80 μM). The conditions of incubation and the MTT assay were as described earlier in this Example. Aβ2–9 reduced ACT activity in promoting the formation of neurotoxic Aβ1–42, 2-2.4-fold Aβ 12–28 and apoE2 decreased apoE4 function in promoting the formation of neurotoxic Aβ1–42 6–9 fold.

The experimental procedure is as described as above in this Example. Each reaction product was applied to carbon coated Formvar on 200 mesh copped grids, washed and negatively stained with 1% uranyl acetate and visualized in a JEOL-100CS electron microscope.

The indicated concentrations of Aβ2–9, Aβ12–28 or apoE2 were incubated with ACT or apoE4 following addition of Aβ1–42 as described earlier in this Example. The reduction of ACT neurotoxic Aβ1–42 promoting activity by Aβ2–9 was detected at 1 nM concentration. The reduction of apoE4 neurotoxic Aβ1–42 promoting activity by Aβ12–28 or apoE2 was observed at 1 nM or 10 nM concentration, respectively.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method of screening for an inhibitor of the formation of Alzheimer β-peptide filaments, comprising the steps of:
   a) combining a compound being assessed for its ability to inhibit the formation of Alzheimer β-peptide filaments, Alzheimer β-peptide and a protein promoting factor, under conditions appropriate for the formation of Alzheimer β-peptide filaments; and
   b) determining whether Alzheimer β-peptide filament formation occurs, wherein if filament formation is less in the presence of the compound than in its absence, the compound is an inhibitor.

2. The method of claim 1, wherein the protein promoting factor is Apolipoprotein E4.

3. A method of screening for an inhibitor of the formation of Alzheimer β-peptide filaments, comprising the steps of:
   a) combining a compound being screened for its ability to inhibit the formation of Alzheimer β-peptide filaments with Alzheimer β-peptide and a protein promoting factor under conditions appropriate for the formation of Alzheimer β-peptide filaments;
   b) combining Alzheimer β-peptide and the protein promoting factor under conditions appropriate for the formation of Alzheimer β-peptide filaments; and
   c) determining the amount of Alzheimer β-peptide filaments formed in a) and in b), wherein less Alzheimer β-peptide filament formation in a) than in b) indicates that the compound being screened is an inhibitor of the formation of the Alzheimer β-peptide filaments.

4. The method of claim 3, wherein the protein promoting factor is Apolipoprotein E4.

5. A method of screening for an inhibitor of the formation of Alzheimer β-peptide filaments, comprising the steps of:
   a) combining Alzheimer β-peptide, $\alpha_1$-antichymotrypsin, and a compound being assessed for its ability to inhibit the formation of Alzheimer β-peptide filaments, under conditions appropriate for the formation of Alzheimer β-peptide filaments; and
   b) determining whether Alzheimer β-peptide filament formation occurs, wherein if filament formation is less in the presence of the compound than in its absence, the compound is an inhibitor.

6. A method of screening for an inhibitor of the formation of Alzheimer β-peptide filaments, comprising the steps of:
   a) combining Alzheimer β-peptide, $\alpha_1$-antichymotrypsin, Apolipoprotein E4, and a compound being assessed for its ability to inhibit the formation of Alzheimer β-peptide filaments, under conditions appropriate for the formation of Alzheimer β-peptide filaments; and
   b) determining whether Alzheimer β-peptide filament formation occurs,
   wherein if filament formation is less in the presence of the compound than in its absence, the compound is an inhibitor.

7. A method of screening for an inhibitor of the formation of Alzheimer β-peptide filaments, comprising the steps of:
   a) combining Alzheimer β-peptide, $\alpha_1$-antichymotrypsin, and a compound being screened for its ability to inhibit the formation of Alzheimer β-peptide filaments under conditions appropriate for the formation of Alzheimer β-peptide filaments;
   b) combining Alzheimer β-peptide and $\alpha_1$-antichymotrypsin under conditions appropriate for the formation of Alzheimer β-peptide filaments; and
   c) determining the amount of Alzheimer β-peptide filaments formed in a) and in b), wherein less Alzheimer β-peptide filament formation in a) than in b) indicates that the compound being screened is an inhibitor of the formation of the Alzheimer β-peptide filaments.

8. A method of screening for an inhibitor of the formation of Alzheimer β-peptide filaments, comprising the steps of: combining Alzheimer β-peptide, $\alpha_1$-anitichymotrypsin, Apolipoprotein E4 and a compound being screened for its ability to inhibit the formation of Alzheimer β-peptide filaments under conditions appropriate for the formation of Alzheimer β-peptide filaments;
   b) combining Alzheimer β-peptide, $\alpha_1$-antichymotrypsin and Apolipoprotein E4 under conditions appropriate for the formation of Alzheimer β-peptide filaments; and
   c) detemining the amount of Alzheimer β-peptide filaments formed in a) and in b), wherein less Alzheimer β-peptide filament formation in a) than in b) indicates that the compound being screened is an inhibitor of the formation of the Alzheimer β-peptide filaments.

* * * * *